United States Patent
Shaheen et al.

(10) Patent No.: US 9,890,378 B2
(45) Date of Patent: Feb. 13, 2018

(54) SURFACE ANCHORED LIGHT CHAIN BAIT ANTIBODY DISPLAY SYSTEM

(71) Applicant: Merck Sharp & Dohme Corp., Rahway, NJ (US)

(72) Inventors: Hussam Hisham Shaheen, Lebanon, NH (US); Dongxing Zha, Lebanon, NH (US)

(73) Assignee: Merck Sharp & Dohme Corp., Rahway, NJ (US)

(*) Notice: Subject to any disclaimer, the term of this patent is extended or adjusted under 35 U.S.C. 154(b) by 221 days.

(21) Appl. No.: 14/399,655

(22) PCT Filed: May 6, 2013

(86) PCT No.: PCT/US2013/039609
§ 371 (c)(1),
(2) Date: Nov. 7, 2014

(87) PCT Pub. No.: WO2013/169609
PCT Pub. Date: Nov. 14, 2013

(65) Prior Publication Data
US 2015/0148246 A1    May 28, 2015

Related U.S. Application Data

(60) Provisional application No. 61/645,763, filed on May 11, 2012.

(51) Int. Cl.
| | | |
|---|---|---|
| C40B 40/02 | (2006.01) | |
| C12N 15/10 | (2006.01) | |
| G01N 33/68 | (2006.01) | |
| C07K 16/00 | (2006.01) | |
| C07K 16/40 | (2006.01) | |
| C07K 14/39 | (2006.01) | |

(52) U.S. Cl.
CPC .......... *C12N 15/1055* (2013.01); *C07K 14/39* (2013.01); *C07K 16/00* (2013.01);
(Continued)

(58) Field of Classification Search
None
See application file for complete search history.

(56) References Cited

U.S. PATENT DOCUMENTS

| | | |
|---|---|---|
| 8,067,339 B2 | 11/2011 | Prinz et al. |
| 8,877,686 B2 | 11/2014 | Zha |

(Continued)

FOREIGN PATENT DOCUMENTS

| | | |
|---|---|---|
| WO | 02057423 A2 | 7/2002 |
| WO | WO2009111183 | 9/2009 |

(Continued)

OTHER PUBLICATIONS

Weaver-Feldhaus, J.M. et al, "Yeast mating for combinatorial, Fab library generation and surface display", FEBS Letters, 564:1-2, (Apr. 23, 2004), pp. 23-34, XP004503587.

(Continued)

*Primary Examiner* — Christian Boesen
(74) *Attorney, Agent, or Firm* — John David Reilly; Gloria Fuentes

(57) ABSTRACT

The present invention provides, in part, an antibody display system that simultaneously uses a secretion and a display mode. Embodiments of the invention provide a system in which a bait complexed with a monovalent antibody fragment can be captured prior to secretion in a host cell by virtue of surface displaying an antibody light chain and utilizing the covalent interaction of this light chain with the heavy chain of an antibody molecule that is co-expressed in the same host. Polypeptides, polynucleotides and host cells useful for making the antibody display system are also provided along with methods of using the system for identifying antibodies that bind specifically to an antigen of interest.

11 Claims, 6 Drawing Sheets

(52) U.S. Cl.
CPC ......... *C07K 16/40* (2013.01); *G01N 33/6854* (2013.01); *G01N 33/6857* (2013.01); *C07K 2317/41* (2013.01); *C07K 2317/52* (2013.01); *C07K 2317/56* (2013.01); *C07K 2319/02* (2013.01); *C07K 2319/035* (2013.01); *C40B 40/02* (2013.01); *G01N 2440/38* (2013.01)

(56) References Cited

U.S. PATENT DOCUMENTS

| | | |
|---|---|---|
| 2006/0134709 A1 | 6/2006 | Stavenhagen et al. |
| 2010/0009866 A1 | 1/2010 | Prinz et al. |
| 2010/0331192 A1 | 12/2010 | Zha et al. |
| 2012/0021948 A1 | 1/2012 | Prinz et al. |

FOREIGN PATENT DOCUMENTS

| | | |
|---|---|---|
| WO | 2010005863 A1 | 1/2010 |
| WO | WO201274948 | 6/2012 |
| WO | WO201343582 | 3/2013 |

OTHER PUBLICATIONS

Shaheen Hussam H et al., "A Dual-Mode Surface Display System for the Maturation and Production of Monoclonal Antibodies in Glyco-Engineered Pichia pastoris", PLOS One, 8:7, (Jul. 2013), XP002750925.

Shaheen et al., A dual-mode surface display system for the maturation and production of monoclonal antibodies in glyco-engineered Pichia pastoris., PLOS One, 2013, 8(7): 1-10, U.S.

ion system that does not suffer from shortcomings of

SEQUENCE LISTING

```
<160> NUMBER OF SEQ ID NOS: 10

<210> SEQ ID NO 1
<211> LENGTH: 322
<212> TYPE: PRT
<213> ORGANISM: Saccharomyces cerevisiae

<400> SEQUENCE: 1

Val Asp Gln Phe Ser Asn Ser Thr Ser Ala Ser Ser Thr Asp Val Thr
1               5                   10                  15

Ser Ser Ser Ile Ser Thr Ser Ser Gly Ser Val Thr Ile Thr Ser
                20                  25                  30

Ser Glu Ala Pro Glu Ser Asp Asn Gly Thr Ser Thr Ala Ala Pro Thr
                35                  40                  45

Glu Thr Ser Thr Glu Ala Pro Thr Thr Ala Ile Pro Thr Asn Gly Thr
            50                  55                  60

Ser Thr Glu Ala Pro Thr Thr Ala Ile Pro Thr Asn Gly Thr Ser Thr
65                  70                  75                  80

Glu Ala Pro Thr Asp Thr Thr Thr Glu Ala Pro Thr Thr Ala Leu Pro
                85                  90                  95

Thr Asn Gly Thr Ser Thr Glu Ala Pro Thr Asp Thr Thr Thr Glu Ala
                100                 105                 110

Pro Thr Thr Gly Leu Pro Thr Asn Gly Thr Thr Ser Ala Phe Pro Pro
                115                 120                 125

Thr Thr Ser Leu Pro Pro Ser Asn Thr Thr Thr Thr Pro Pro Tyr Asn
            130                 135                 140

Pro Ser Thr Asp Tyr Thr Thr Asp Tyr Thr Val Val Thr Glu Tyr Thr
145                 150                 155                 160

Thr Tyr Cys Pro Glu Pro Thr Thr Phe Thr Thr Asn Gly Lys Thr Tyr
                165                 170                 175

Thr Val Thr Glu Pro Thr Thr Leu Thr Ile Thr Asp Cys Pro Cys Thr
                180                 185                 190

Ile Glu Lys Pro Thr Thr Thr Ser Thr Thr Glu Tyr Thr Val Val Thr
                195                 200                 205

Glu Tyr Thr Thr Tyr Cys Pro Glu Pro Thr Thr Phe Thr Thr Asn Gly
            210                 215                 220

Lys Thr Tyr Thr Val Thr Glu Pro Thr Thr Leu Thr Ile Thr Asp Cys
225                 230                 235                 240

Pro Cys Thr Ile Glu Lys Ser Glu Ala Pro Glu Ser Ser Val Pro Val
                245                 250                 255

Thr Glu Ser Lys Gly Thr Thr Thr Lys Glu Thr Gly Val Thr Thr Lys
                260                 265                 270
```

```
Gln Thr Thr Ala Asn Pro Ser Leu Thr Val Ser Thr Val Pro Val
        275                 280                 285

Ser Ser Ser Ala Ser Ser His Ser Val Val Ile Asn Ser Asn Gly Ala
    290                 295                 300

Asn Val Val Pro Gly Ala Leu Gly Leu Ala Gly Val Ala Met Leu
305             310                 315                 320

Phe Leu

<210> SEQ ID NO 2
<211> LENGTH: 960
<212> TYPE: DNA
<213> ORGANISM: Pichia pastoris

<400> SEQUENCE: 2
caattctcta actctacttc cgcttcctct actgacgtta cttcctcctc ctctatttct      60
acttcctccg gttccgttac tattacttcc tctgaggctc agaatctgaa caacggtact     120
tctactgctg ctccaactga aacttctact gaggctccta ctactgctat tccaactaac     180
ggaacttcca cagaggctcc aacaacagct atccctacaa acggtacatc cactgaagct     240
cctactgaca ctactacaga agctccaact actgctttgc ctactaatgg tacatcaaca     300
gaggctccta cagatacaac aactgaagct ccaacaactg gattgccaac aaacggtact     360
acttctgctt tcccaccaac tacttccttg ccaccatcca acactactac tactccacca     420
tacaacccat ccactgacta cactactgac tacacagttg ttactgagta cactacttac     480
tgtccagagc caactacttt cacaacaaac ggaaagactt acactgttac tgagcctact     540
actttgacta tcactgactg tccatgtact atcgagaagc aactactac ttccactaca     600 gagtatactg ttgttacaga atacacaaca tattgtcctg agccaacaac attcactact     660
aatggaaaaa catacacagt tacagaacca actacattga caattacaga ttgtccttgt     720
acaattgaga agtccgaggc tcctgaatct tctgttccag ttactgaatc caagggtact     780
actactaaag aaactggtgt tactactaag cagactactg ctaacccatc cttgactgtt     840
tccactgttg ttccagtttc ttcctctgct tcttcccact ccgttgttat caactccaac     900
ggtgctaacg ttgttgttcc tggtgctttg ggattggctg tgttgctat gttgttcttg     960

<210> SEQ ID NO 3
<211> LENGTH: 19
<212> TYPE: PRT
<213> ORGANISM: Saccharomyces cerevisiae

<400> SEQUENCE: 3

Met Arg Phe Pro Ser Ile Phe Thr Ala Val Leu Phe Ala Ala Ser Ser
1               5                   10                  15

Ala Leu Ala

<210> SEQ ID NO 4
<211> LENGTH: 57
<212> TYPE: DNA
<213> ORGANISM: Saccharomyces cerevisiae

<400> SEQUENCE: 4
atgagattcc catccatctt cactgctgtt ttgttcgctg cttcctctgc tttggct         57

<210> SEQ ID NO 5
<211> LENGTH: 551
<212> TYPE: PRT
<213> ORGANISM: Artificial Sequence
```

<220> FEATURE:
<223> OTHER INFORMATION: human light chain immunoglobulin domain fused to a Pichia pastoris Sed1p polypeptide

<400> SEQUENCE: 5

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Val Trp Tyr Gln Gln Lys Pro Gly Lys Ala Pro Lys Ala Leu Ile
        35                  40                  45

His Ser Ala Ser Tyr Arg Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Lys Thr Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Gly Gly Gly Gly Ser
210                 215                 220

Gly Gly Gly Gly Ser Val Asp Gln Phe Ser Asn Ser Thr Ser Ala Ser
225                 230                 235                 240

Ser Thr Asp Val Thr Ser Ser Ser Ile Ser Thr Ser Ser Gly Ser
                245                 250                 255

Val Thr Ile Thr Ser Ser Glu Ala Pro Glu Ser Asp Asn Gly Thr Ser
            260                 265                 270

Thr Ala Ala Pro Thr Glu Thr Ser Thr Glu Ala Pro Thr Thr Ala Ile
        275                 280                 285

Pro Thr Asn Gly Thr Ser Thr Glu Ala Pro Thr Thr Ala Ile Pro Thr
290                 295                 300

Asn Gly Thr Ser Thr Glu Ala Pro Thr Asp Thr Thr Glu Ala Pro
305                 310                 315                 320

Thr Thr Ala Leu Pro Thr Asn Gly Thr Ser Thr Glu Ala Pro Thr Asp
                325                 330                 335

Thr Thr Thr Glu Ala Pro Thr Thr Gly Leu Pro Thr Asn Gly Thr Thr
            340                 345                 350

Ser Ala Phe Pro Pro Thr Thr Ser Leu Pro Pro Ser Asn Thr Thr Thr
        355                 360                 365

Thr Pro Pro Tyr Asn Pro Ser Thr Asp Tyr Thr Thr Asp Tyr Thr Val
370                 375                 380

Val Thr Glu Tyr Thr Thr Tyr Cys Pro Glu Pro Thr Thr Phe Thr Thr
```

```
                385                 390                 395                 400
Asn Gly Lys Thr Tyr Thr Val Thr Glu Pro Thr Thr Leu Thr Ile Thr
            405                 410                 415

Asp Cys Pro Cys Thr Ile Glu Lys Pro Thr Thr Ser Thr Thr Glu
            420                 425                 430

Tyr Thr Val Thr Glu Tyr Thr Thr Tyr Cys Pro Glu Pro Thr Thr
            435                 440                 445

Phe Thr Thr Asn Gly Lys Thr Tyr Thr Val Glu Pro Thr Thr Leu
    450                 455                 460

Thr Ile Thr Asp Cys Pro Cys Thr Ile Glu Lys Ser Glu Ala Pro Glu
465                 470                 475                 480

Ser Ser Val Pro Val Thr Glu Ser Lys Gly Thr Thr Lys Glu Thr
                485                 490                 495

Gly Val Thr Thr Lys Gln Thr Thr Ala Asn Pro Ser Leu Thr Val Ser
                500                 505                 510

Thr Val Val Pro Val Ser Ser Ala Ser Ser His Ser Val Val Ile
            515                 520                 525

Asn Ser Asn Gly Ala Asn Val Val Pro Gly Ala Leu Gly Leu Ala
    530                 535                 540

Gly Val Ala Met Leu Phe Leu
545                 550

<210> SEQ ID NO 6
<211> LENGTH: 1647
<212> TYPE: DNA
<213> ORGANISM: Artificial Sequence
<220> FEATURE:
<223> OTHER INFORMATION: human light chain immunoglobulin domain fused
      to a Pichia pastoris Sed1p polypeptide

<400> SEQUENCE: 6
gacattcaaa tgactcagtc cccatcttcc ttgtctgctt ccgttggtga cagagttact      60
atcacttgta aggcttccca gaacgttgga actaacgttg tttggtatca gcagaagcca     120
ggtaaggctc caaaggcttt gattcactcc gcttcataca gatactccgg tgttccatcc     180
agattctctg gttctggttc cggtactgac tttactttga ctatctcctc attgcagcca     240
gaggacttcg ctacttacta ctgtcagcag tacaagactt acccatacac tttcggtcag     300
ggtaccaagg ttgagatcaa agaactgttg ctgctccat ccgttttcat tttcccacca     360
tccgacgaac agttgaagtc tggtacagct tccgttgttt gtttgttgaa caacttctac     420
ccaagagagg ctaaggttca gtggaaggtt gacaacgctt tgcaatccgg taactcccaa     480
gaatccgtta ctgagcaaga ctctaaggac tccacttact ccttgtcctc cactttgact     540
ttgtccaagg ctgattacga aagcacaag gtttacgctt gtgaggttac acatcagggt     600
ttgtcctccc cagttactaa gtccttcaac agaggagagt gtggtggtgg tggttccggt     660
ggtggtggtt ctggtggtgg tggttctcaa ttctctaact ctacttccgc ttcctctact     720
gacgttactt cctcctcctc tatttctact tcctccggtt ccgttactat tacttcctct     780
gaggctccag aatctgacaa cggtacttct actgctgctc caactgaaac ttctactgag     840
gctcctacta ctgctattcc aactaacgga acttccacag aggctccaac aacagctatc     900
cctacaaacg gtacatccac tgaagctcct actgacacta ctacagaagc tccaactact     960
gctttgccta ctaatggtac atcaacagag gctcctacag atacaacaac tgaagctcca    1020
acaactggat tgccaacaaa cggtactact tctgctttcc caccaactac ttccttgcca    1080
```

```
ccatccaaca ctactactac tccaccatac aacccatcca ctgactacac tactgactac    1140
acagttgtta ctgagtacac tacttactgt ccagagccaa ctactttcac aacaaacgga    1200
aagacttaca ctgttactga gcctactact ttgactatca ctgactgtcc atgtactatc    1260
gagaagccaa ctactacttc cactacagag tatactgttg ttacagaata cacaacatat    1320
tgtcctgagc aacaacatt cactactaat ggaaaaacat acacagttac agaaccaact    1380
acattgacaa ttacagattg tccttgtaca attgagaagt ccgaggctcc tgaatcttct    1440
gttccagtta ctgaatccaa gggtactact actaagaaa ctggtgttac tactaagcag    1500
actactgcta acccatcctt gactgtttcc actgttgttc cagtttcttc ctctgcttct    1560
tcccactccg ttgttatcaa ctccaacggt gctaacgttg ttgttcctgg tgctttggga    1620
ttggctggtg ttgctatgtt gttcttg                                        1647

<210> SEQ ID NO 7
<211> LENGTH: 9180
<212> TYPE: DNA
<213> ORGANISM: Artificial Sequence
<220> FEATURE:
<223> OTHER INFORMATION: pGLY11714

<400> SEQUENCE: 7
tcgcgcgttt cggtgatgac ggtgaaaacc tctgacacat gcagctcccg gagacggtca      60
cagcttgtct gtaagcggat gccgggagca gacaagcccg tcaggcgcg tcagcgggtg     120 ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt gagatctaac atccaaagac     420
gaaaggttga atgaaacctt tttgccatcc gacatccaca ggtccattct cacacataag     480
tgccaaacgc aacaggaggg gatacactag cagcagaccg ttgcaaacgc aggacctcca     540
ctcctcttct cctcaacacc cacttttgcc atcgaaaaac cagcccagtt attgggcttg     600
attggagctc gctcattcca attccttcta ttaggctact aacaccatga ctttattagc     660
ctgtctatcc tggccccccct ggcgaggttc atgtttgttt atttccgaat gcaacaagct     720
ccgcattaca cccgaacatc actccagatg agggctttct gagtgtgggg tcaaatagtt     780
tcatgttccc caaatggccc aaaactgaca gtttaaacgc tgtcttggaa cctaatatga     840
caaaagcgtg atctcatcca agatgaacta agtttggttc gttgaaatgc taacggccag     900
ttggtcaaaa agaaacttcc aaaagtcggc ataccgtttg tcttgtttgg tattgattga     960
cgaatgctca aaaataatct cattaatgct tagcgcagtc tctctatcgc ttctgaaccc    1020
cggtgcacct gtgccgaaac gcaaatgggg aaacacccgc ttttggatg attatgcatt    1080 gtctccacat tgtatgcttc caagattctg gtgggaatac tgctgatagc ctaacgttca    1140
tgatcaaaat ttaactgttc taaccccta cttgacagcaa tatataaaca gaaggaagct    1200
gccctgtctt aaacctttt ttttatcatc attattagct tactttcata attgcgactg    1260
gttccaattg acaagctttt gattttaacg acttttaacg acaacttgag aagatcaaaa    1320
aacaactaat tattcgaaac ggaattcacg atgagattcc catccatctt cactgctgtt    1380
ttgttcgctg cttcctctgc tttggctgac attcaaatga ctcagtcccc atcttccttg    1440
tctgcttccg ttggtgacag agttactatc acttgtaagg cttcccagaa cgttggaact    1500
```

```
aacgttgttt ggtatcagca gaagccaggt aaggctccaa aggctttgat tcactccgct    1560
tcatacagat actccggtgt tccatccaga ttctctggtt ctggttccgg tactgacttt    1620
actttgacta tctcctcatt gcagccagag gacttcgcta cttactactg tcagcagtac    1680
aagacttacc catacacttt cggtcagggt accaaggttg agatcaagag aactgttgct    1740
gctccatccg ttttcatttt cccaccatcc gacgaacagt tgaagtctgg tacagcttcc    1800
gttgtttgtt tgttgaacaa cttctaccca agagaggcta aggttcagtg gaaggttgac    1860
aacgctttgc aatccggtaa ctcccaagaa tccgttactg agcaagactc taaggactcc    1920
acttactcct tgtcctccac tttgactttg tccaaggctg attacgagaa gcacaaggtt    1980
tacgcttgtg aggttacaca tcagggtttg tcctccccag ttactaagtc cttcaacaga    2040
ggagagtgtg tggtggtggt ttccggtggt ggtggttctg tggtggtggg ttctgtcgac    2100
caattctcta actctacttc cgcttcctct actgacgtta cttcctcctc ctctatttct    2160
acttcctccg gttccgttac tattacttcc tctgaggctc cagaatctga caacggtact    2220
tctactgctg ctccaactga aacttctact gaggctccta ctactgctat tccaactaac    2280
ggaacttcca cagaggctcc aacaacagct atccctacaa acggtacatc cactgaagct    2340
cctactgaca ctactacaga agctccaact actgctttgc ctactaatgg tacatcaaca    2400
gaggctccta cagatacaac aactgaagct ccaacaactg gattgccaac aaacggtact    2460
acttctgctt tcccaccaac tacttccttg ccaccatcca acactactac tactccacca    2520
tacaacccat ccactgacta cactactgac tacacagttg ttactgagta cactacttac    2580
tgtccagagc caactacttt cacaacaaac ggaaagactt acactgttac tgagcctact    2640
actttgacta tcactgactg tccatgtact atcgagaagc caactactac ttccactaca    2700
gagtatactg ttgttacaga atacacaaca tattgtcctg agccaacaac attcactact    2760
aatggaaaaa catacacagt tacagaacca actacattga caattacaga ttgtccttgt    2820
acaattgaga agtccgaggc tcctgaatct tctgttccag ttactgaatc caagggtact    2880
actactaaag aaactggtgt tactactaag cagactactg ctaacccatc cttgactgtt    2940
tccactgttg ttccagtttc ttcctctgct tcttcccact ccgttgttat caactccaac    3000
ggtgctaacg ttgttgttcc tggtgctttg ggattggctg tgttgctat gttgttcttg    3060 taatagggcc ggccatttaa atacaggccc cttttccttt gtcgatatca tgtaattagt    3120
tatgtcacgc ttacattcac gccctcctcc cacatccgct ctaaccgaaa aggaaggagt    3180
tagacaacct gaagtctagg tccctatttta ttttttttaa tagttatgtt agtattaaga    3240
acgttattta tatttcaaat ttttctttttt tttctgtaca aacgcgtgta cgcatgtaac    3300
attatactga aaaccttgct tgagaaggtt ttgggacgct cgaaggcttt aatttgcaag    3360
ctggatccgc ggccgcttac gcgccgttct tcgcttggtc ttgtatctcc ttacactgta    3420
tcttcccatt tgcgtttagg tggttatcaa aaactaaaag gaaaaatttc agatgtttat    3480
ctctaaggtt ttttctttttt acagtataac acgtgatgcg tcacgtggta ctagattacg    3540
taagttattt tggtccggtg ggtaagtggg taagaataga aagcatgaag gtttacaaaa    3600
acgcagtcac gaattattgc tacttcgagc ttggaaccac cccaaagatt atattgtact    3660
gatgcactac cttctcgatt tgctcctcc aagaacctac gaaaaacatt tcttgagcct    3720
tttcaaccta gactacacat caagttattt aaggtatgtt ccgttaacat gtaagaaaag    3780
gagaggatag atcgtttatg gggtacgtcg cctgattcaa gcgtgaccat tcgaagaata    3840
```

```
ggccttcgaa agctgaataa agcaaatgtc agttgcgatt ggtatgctga caaattagca      3900
taaaaagcaa tagactttct aaccaccgtg ttttttcctt ttactttatt tatatttgc      3960 caccgtacta acaagttcag acaaattaat taacaccatg tcagaagatc aaaaaagtga      4020
aaattccgta ccttctaagg ttaatatggt gaatcgcacc gatatactga ctacgatcaa      4080
gtcattgtca tggcttgact tgatgttgcc atttactata attctctcca taatcattgc      4140
agtaataatt tctgtctatg tgccttcttc ccgtcacact tttgacgctg aaggtcatcc      4200
caatctaatg ggagtgtcca ttcctttgac tgttggtatg attgtaatga tgattccccc      4260
gatctgcaaa gtttcctggg agtctattca caagtacttc tacaggagct atataaggaa      4320
gcaactagcc ctctcgttat ttttgaattg ggtcatcggt cctttgttga tgacagcatt      4380
ggcgtggatg gcgctattcg attataagga ataccgtcaa ggcattatta tgatcggagt      4440
agctagatgc attgccatgg tgctaatttg gaatcagatt gctggaggag acaatgatct      4500
ctgcgtcgtg cttgttatta caaactcgct tttacagatg gtattatatg caccattgca      4560
gatattttac tgttatgtta tttctcatga ccacctgaat acttcaaata gggtattatt      4620
cgaagaggtt gcaaagtctg tcggagtttt tctcggcata ccactgggaa ttggcattat      4680
catacgtttg ggagtctta ccatagctgg taaaagtaat tatgaaaaat acattttgag      4740
atttatttct ccatgggcaa tgatcggatt tcattacact ttatttgtta tttttattag      4800
tagaggttat caatttatcc acgaaattgg ttctgcaata ttgtgctttg tcccattggt      4860
gctttacttc tttattgcat ggttttgac cttcgcatta atgaggtact tatcaatatc      4920
taggagtgat acacaaagag aatgtagctg tgaccaagaa ctacttttaa agagggtctg      4980
gggaagaaag tcttgtgaag ctagctttc tattacgatg acgcaatgtt tcactatggc      5040
ttcaaataat tttgaactat ccctggcaat tgctatttcc ttatatggta acaatagcaa      5100
gcaagcaata gctgcaacat ttgggccgtt gctagaagtt ccaattttat tgattttggc      5160
aatagtcgcg agaatcctta aaccatatta tatatgaac aatagaaatt aattaacagg      5220
ccccttttcc tttgtcgata tcatgtaatt agttatgtca cgcttacatt cacgccctcc      5280
tcccacatcc gctctaaccg aaaaggaagg agttagacaa cctgaagtct aggtccctat      5340
ttattttttt taatagttat gttagtatta agaacgttat ttatatttca aattttctt      5400 ttttttctgt acaaacgcgt gtacgcatgt aacattatac tgaaaacctt gcttgagaag      5460
gttttgggac gctcgaaggc tttaatttgc aagctgcggc ctaaggcgcg ccaggccata      5520
atggcccaaa tgcaagagga cattagaaat gtgtttggta agaacatgaa gccggaggca      5580
tacaaacgat tcacagattt gaaggaggaa acaaactgc atccaccgga agtgccagca      5640
gccgtgtatg ccaaccttgc tctcaaaggc attcctacgg atctgagtgg gaaatatctg      5700
agattcacag acccactatt ggaacagtac caaacctagt ttggccgatc catgattatg      5760
taatgcatat agttttttgtc gatgctcacc cgtttcgagt ctgtctcgta tcgtcttacg      5820
tataagttca agcatgttta ccaggtctgt tagaaactcc tttgtgaggg caggacctat      5880
tcgtctcggt cccgttgttt ctaagagact gtacagccaa gcgcagaatg gtggcattaa      5940
ccataagagg attctgatcg gacttggtct attggctatt ggaaccaccc tttacgggac      6000
aaccaaccct accaagactc ctattgcatt tgtggaacca gccacggaaa gagcgtttaa      6060
ggacggagac gtctctgtga ttttgttct cggaggtcca ggagctggaa aaggtaccca      6120
atgtgccaaa ctagtgagta attacggatt tgttcacctg tcagctggag acttgttacg      6180
tgcagaacag aagagggagg ggtctaagta tggagagatg atttcccagt atatcagaga      6240
```

```
tggactgata gtacctcaag aggtcaccat tgcgctcttg gagcaggcca tgaaggaaaa    6300
cttcgagaaa gggaagacac ggttcttgat tgatggattc cctcgtaaga tggaccaggc    6360
caaaactttt gaggaaaaag tcgcaaagtc caaggtgaca cttttctttg attgtcccga    6420
atcagtgctc cttgagagat tacttaaaag aggacagaca agcggaagag aggatgataa    6480
tgcggagagt atcaaaaaaa gattcaaaac attcgtggaa acttcgatgc ctgtggtgga    6540
ctatttcggg aagcaaggac gcgttttgaa ggtatcttgt gaccaccctg tggatcaagt    6600
gtattcacag gttgtgtcgg tgctaaaaga aaggggatc tttgccgata acgagacgga    6660
gaataaataa acattgtaat aagatttaga ctgtgaatgt tctatgtaat attttcgag    6720 atactgtatc tatctggtgt accgtatcac tctggacttg caaactcatt gattacttgt    6780
gcaatgggca agaaggatag ctctagaaag aagaagaaaa aggagccgcc tgaagagctg    6840
gatctttccg aggttgttcc aacttttggt tatgaggaat tcatgttga gcaagaggag    6900 aatccggtcg atcaagacga acttgacggc ataatggcc tagcttggcg taatcatggt    6960
catagctgtt tcctgtgtga aattgttatc cgctcacaat tccacacaac atacgagccg    7020
gaagcataaa gtgtaaagcc tggggtgcct aatgagtgag ctaactcaca ttaattgcgt    7080
tgcgctcact gcccgctttc cagtcgggaa acctgtcgtg ccagctgcat taatgaatcg    7140
gccaacgcgc ggggagaggc ggtttgcgta ttgggcgctc ttccgcttcc tcgctcactg    7200
actcgctgcg ctcggtcgtt cggctgcggc gagcggtatc agctcactca aaggcggtaa    7260
tacggttatc cacagaatca ggggataacg caggaaagaa catgtgagca aaaggccagc    7320
aaaaggccag gaaccgtaaa aaggccgcgt tgctggcgtt tttccatagg ctccgccccc    7380
ctgacgagca tcacaaaaat cgacgctcaa gtcagaggtg gcgaaacccg acaggactat    7440
aaagatacca ggcgtttccc cctggaagct ccctcgtgcg ctctcctgtt ccgaccctgc    7500
cgcttaccgg atacctgtcc gcctttctcc cttcgggaag cgtggcgctt tctcatagct    7560
cacgctgtag gtatctcagt tcggtgtagg tcgttcgctc caagctgggc tgtgtgcacg    7620 aacccccgt tcagcccgac cgctgcgcct tatccggtaa ctatcgtctt gagtccaacc    7680
cggtaagaca cgacttatcg ccactggcag cagccactgg taacaggatt agcagagcga    7740
ggtatgtagg cggtgctaca gagttcttga agtggtggcc taactacggc tacactagaa    7800
ggacagtatt tggtatctgc gctctgctga agccagttac cttcggaaaa agagttggta    7860
gctcttgatc cggcaaacaa accaccgctg gtagcggtgg tttttttgtt tgcaagcagc    7920
agattacgcg cagaaaaaaa ggatctcaag aagatccttt gatcttttct acggggtctg    7980
acgctcagtg gaacgaaaac tcacgttaag ggattttggt catgagatta tcaaaaagga    8040
tcttcaccta gatccttta aattaaaaat gaagttttaa atcaatctaa agtatatatg    8100
agtaaacttg gtctgacagt taccaatgct taatcagtga ggcacctatc tcagcgatct    8160
gtctatttcg ttcatccata gttgcctgac tccccgtcgt gtagataact acgatacggg    8220
agggcttacc atctggcccc agtgctgcaa tgataccgcg agacccacgc tcaccggctc    8280
cagatttatc agcaataaac cagccagccg gaagggccga gcgcagaagt ggtcctgcaa    8340
ctttatccgc ctccatccag tctattaatt gttgccggga agctagagta agtagttcgc    8400
cagttaatag tttgcgcaac gttgttgcca ttgctacagg catcgtggtg tcacgctcgt    8460
cgtttggtat ggcttcattc agctccggtt cccaacgatc aaggcgagtt acatgatccc    8520
ccatgttgtg caaaaaagcg gttagctcct tcggtcctcc gatcgttgtc agaagtaagt    8580
```

-continued

```
tggccgcagt gttatcactc atggttatgg cagcactgca taattctctt actgtcatgc    8640
catccgtaag atgctttcct gtgactggtg agtactcaac caagtcattc tgagaatagt    8700
gtatgcggcg accgagttgc tcttgcccgg cgtcaatacg ggataatacc gcgccacata    8760
gcagaacttt aaaagtgctc atcattggaa aacgttcttc ggggcgaaaa ctctcaagga    8820
tcttaccgct gttgagatcc agttcgatgt aacccactcg tgcacccaac tgatcttcag    8880
catcttttac tttcaccagc gtttctgggt gagcaaaaac aggaaggcaa atgccgcaa     8940 aaagggaat aagggcgaca cggaaatgtt gaatactcat actcttcctt tttcaatatt    9000
attgaagcat ttatcagggt tattgtctca tgagcggata catatttgaa tgtatttaga    9060
aaaataaaca ataggggtt ccgcgcacat ttccccgaaa agtgccacct gacgtctaag     9120
aaaccattat tatcatgaca ttaacctata aaaataggcg tatcacgagg ccctttcgtc    9180
```

```
<210> SEQ ID NO 8
<211> LENGTH: 214
<212> TYPE: PRT
<213> ORGANISM: Artificial Sequence
<220> FEATURE:
<223> OTHER INFORMATION: Humanized mouse Ig

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Val Trp Tyr Gln Gln Lys Pro Gly Lys Ala Pro Lys Ala Leu Ile
        35                  40                  45

His Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Lys Thr Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 9
<211> LENGTH: 570
<212> TYPE: PRT
<213> ORGANISM: Artificial Sequence
<220> FEATURE:
<223> OTHER INFORMATION: Amino acid sequence of alpha mating factor-
``` antipPCSK9 Lc-(GGGS) linker-S. cerevisiae Sed1p

<400> SEQUENCE: 9

```
Met Arg Phe Pro Ser Ile Phe Thr Ala Val Leu Phe Ala Ala Ser Ser
 1               5                  10                  15
Ala Leu Ala Asp Ile Gln Met Thr Gln Ser Pro Ser Ser Leu Ser Ala
            20                  25                  30
Ser Val Gly Asp Arg Val Thr Ile Thr Cys Lys Ala Ser Gln Asn Val
        35                  40                  45
Gly Thr Asn Val Val Trp Tyr Gln Gln Lys Pro Gly Lys Ala Pro Lys
    50                  55                  60
Ala Leu Ile His Ser Ala Ser Tyr Arg Tyr Ser Gly Val Pro Ser Arg
65                  70                  75                  80
Phe Ser Gly Ser Gly Ser Gly Thr Asp Phe Thr Leu Thr Ile Ser Ser
                85                  90                  95
Leu Gln Pro Glu Asp Phe Ala Thr Tyr Tyr Cys Gln Gln Tyr Lys Thr
            100                 105                 110
Tyr Pro Tyr Thr Phe Gly Gln Gly Thr Lys Val Glu Ile Lys Arg Thr
        115                 120                 125
Val Ala Ala Pro Ser Val Phe Ile Phe Pro Pro Ser Asp Glu Gln Leu
    130                 135                 140
Lys Ser Gly Thr Ala Ser Val Val Cys Leu Leu Asn Asn Phe Tyr Pro
145                 150                 155                 160
Arg Glu Ala Lys Val Gln Trp Lys Val Asp Asn Ala Leu Gln Ser Gly
                165                 170                 175
Asn Ser Gln Glu Ser Val Thr Glu Gln Asp Ser Lys Asp Ser Thr Tyr
            180                 185                 190
Ser Leu Ser Ser Thr Leu Thr Leu Ser Lys Ala Asp Tyr Glu Lys His
        195                 200                 205
Lys Val Tyr Ala Cys Glu Val Thr His Gln Gly Leu Ser Ser Pro Val
    210                 215                 220
Thr Lys Ser Phe Asn Arg Gly Glu Cys Gly Gly Gly Gly Ser Gly Gly
225                 230                 235                 240
Gly Gly Ser Gly Gly Gly Ser Val Asp Gln Phe Ser Asn Ser Thr
                245                 250                 255
Ser Ala Ser Ser Thr Asp Val Thr Ser Ser Ser Ser Ile Ser Thr Ser
            260                 265                 270
Ser Gly Ser Val Thr Ile Thr Ser Ser Glu Ala Pro Glu Ser Asp Asn
        275                 280                 285
Gly Thr Ser Thr Ala Ala Pro Thr Glu Thr Ser Thr Glu Ala Pro Thr
    290                 295                 300
Thr Ala Ile Pro Thr Asn Gly Thr Ser Thr Glu Ala Pro Thr Thr Ala
305                 310                 315                 320
Ile Pro Thr Asn Gly Thr Ser Thr Glu Ala Pro Thr Asp Thr Thr Thr
                325                 330                 335
Glu Ala Pro Thr Thr Ala Leu Pro Thr Asn Gly Thr Ser Thr Glu Ala
            340                 345                 350
Pro Thr Asp Thr Thr Thr Glu Ala Pro Thr Gly Leu Pro Thr Asn
        355                 360                 365
Gly Thr Thr Ser Ala Phe Pro Pro Thr Thr Ser Leu Pro Pro Ser Asn
    370                 375                 380
Thr Thr Thr Thr Pro Pro Tyr Asn Pro Ser Thr Asp Tyr Thr Thr Asp
385                 390                 395                 400
```

```
Tyr Thr Val Val Thr Glu Tyr Thr Thr Tyr Cys Pro Glu Pro Thr Thr
                405                 410                 415

Phe Thr Thr Asn Gly Lys Thr Tyr Thr Val Thr Glu Pro Thr Thr Leu
            420                 425                 430

Thr Ile Thr Asp Cys Pro Cys Thr Ile Glu Lys Pro Thr Thr Thr Ser
        435                 440                 445

Thr Thr Glu Tyr Thr Val Val Thr Glu Tyr Thr Thr Tyr Cys Pro Glu
    450                 455                 460

Pro Thr Thr Phe Thr Thr Asn Gly Lys Thr Tyr Thr Val Thr Glu Pro
465                 470                 475                 480

Thr Thr Leu Thr Ile Thr Asp Cys Pro Cys Thr Ile Glu Lys Ser Glu
                485                 490                 495

Ala Pro Glu Ser Ser Val Pro Val Thr Glu Ser Lys Gly Thr Thr Thr
            500                 505                 510

Lys Glu Thr Gly Val Thr Thr Lys Gln Thr Thr Ala Asn Pro Ser Leu
        515                 520                 525

Thr Val Ser Thr Val Val Pro Val Ser Ser Ser Ala Ser Ser His Ser
    530                 535                 540

Val Val Ile Asn Ser Asn Gly Ala Asn Val Val Val Pro Gly Ala Leu
545                 550                 555                 560

Gly Leu Ala Gly Val Ala Met Leu Phe Leu
                565                 570

<210> SEQ ID NO 10
<211> LENGTH: 4
<212> TYPE: PRT
<213> ORGANISM: Artificial Sequence
<220> FEATURE:
<223> OTHER INFORMATION: linker

<400> SEQUENCE: 10

Gly Gly Gly Ser
1
```

SURFACE ANCHORED LIGHT CHAIN BAIT ANTIBODY DISPLAY SYSTEM This application claims the benefit of U.S. Provisional Patent Application No. 61/645,763, filed May 11, 2012, which is herein incorporated by reference in its entirety.

FIELD OF THE INVENTION

The field of the invention relates to antibody display systems and methods of use for identifying antibodies that bind specifically to an antigen.

BACKGROUND OF THE INVENTION

Phage display is a well-known technique for constructing and screening antibody libraries, whereby the protein of interest is expressed as a polypeptide fusion to a bacteriophage coat protein and subsequently screened by binding to immobilized or soluble biotinylated ligand. Traditional phage display, however, has several shortcomings. For example, some eukaryotic secreted proteins and cell surface proteins require post-translational modifications such as glycosylation or extensive disulfide isomerization, which are unavailable in bacterial cells.

Current yeast surface antibody display systems, such as cold capture, also suffer from various drawbacks. In the cold capture antibody display system, at low temperatures, the process of antibody release from host cell transport vesicles is delayed, so that the secreted antibody can be assayed on the cell surface for antigen binding. The cold capture method suffers from a low signal-to-noise ratio and identification of an antibody with specificity for the target antigen depends heavily on cellular expression levels of the antibody.

The affinity matrix system couples antibodies to the host cell surface, e.g., by biotin, where they can be assayed for antigen binding. The affinity matrix system exhibits a high incidence of cross-contamination between antibody clones. Antibodies may become decoupled from the host cell and, thus lose their link to the polynucleotides encoding their immunoglobulin chains.

Full length antibody display systems tether the full length antibody on the host cell surface by binding an immunoglobulin binding protein, such as protein A, that is fused to a cell surface anchor protein. The host cell contains polynucleotides encoding the antibody immunoglobulin chains. Typically, binding of the antibody occurs after the immunoglobulin binding protein is expressed on the cell surface. This system, thus, leads to some erroneous binding of the antibody to host cells that do not express the antibody. The present system and methods provide numerous advantages over these earlier methods.

SUMMARY OF THE INVENTION

The present invention provides, in part, an antibody display system that does not suffer from shortcomings of currently available systems. This display system allows for the discovery of novel Fc variants that possess specific desired biological properties, such as Fc receptor binding affinities. It also allows for engineering of the Fab region. Previous methods relied on capturing antibodies on the cell surface following secretion in culture medium. Methods and capture systems of the present invention avoid cross-contamination between clones within the same culture by capturing the antibody prior to secretion. Advantageously, embodiments of the present invention allow co-secretion of the displayed molecule allowing further in vitro analysis.

The present invention provides an antibody display system comprising:
(a) an isolated host cell;
(b) a bait comprising a light immunoglobulin chain or functional fragment thereof fused to a surface anchor polypeptide or functional fragment thereof;
(c) one or more polynucleotides encoding an immunoglobulin light chain variable region; and
(d) one or more polynucleotides encoding an immunoglobulin heavy chain variable region.

Optionally, the antibody display system further comprises:
(i) a non-tethered full antibody or antigen-binding fragment thereof comprising said immunoglobulin light and heavy chains encoded by said polynucleotides; and/or
(ii) a monovalent antibody fragment which is complexed with an immunoglobulin heavy chain which is complexed with the immunoglobulin light chain of the bait.

In an embodiment of the invention, said one or more polynucleotides encoding an immunoglobulin light chain is from a genetically diverse population of immunoglobulin light chains; and/or, said one or more polynucleotides encoding an immunoglobulin heavy chain is from a genetically diverse population of immunoglobulin heavy chains.

In yet an additional embodiment of the invention, the host cell comprises a polynucleotide encoding the bait which is operably associated with a regulatable promoter.

In certain embodiments, the host cell is a *Pichia* cell or a *Saccharomyces cerevisiae* cell.

The present invention also provides an isolated bait polypeptide comprising a light immunoglobulin chain or functional fragment thereof fused, optionally by a peptide linker, to a surface anchor polypeptide or a functional fragment thereof; which bait polypeptide is optionally amino-terminally fused to a signal peptide. The bait polypeptide includes the surface anchor polypeptide is SED-1 or a functional fragment thereof. In certain embodiments, the light immunoglobulin chain or functional fragment thereof comprises a kappa or lambda constant immunoglobulin domain.

Any isolated polynucleotide encoding any of the polypeptides; vectors including the polynucleotides and isolated host cells comprising the polynucleotides and vectors are encompassed by the present invention. Additionally, the present invention includes an isolated host cell (e.g., a eukaryotic host cell (including Chinese hamster ovary cells, i.e., CHO cells), also including a lower eukaryotic yeast or filamentous fungi host cell, such as a *Pichia*, e.g., *Pichia pastoris* cell) further comprising one or more polynucleotides encoding an immunoglobulin light chain; and/or one or more polynucleotides encoding an immunoglobulin heavy chain. In certain embodiments, the bait polypeptide is located on the surface of the cell membrane.

The present invention also provides a composition comprising the host cell of any one of the present invention (see e.g., above), further comprising a non-tethered full antibody or antigen-binding fragment thereof comprising said immunoglobulin light and heavy chains; and/or a bait/antigen-binding fragment or bait/antibody; optionally, complexed with an antigen.

The present invention also provides a method for determining if an antibody or antigen-binding fragment thereof, secreted from a host cell, specifically binds to an antigen comprising contacting an antibody display system with said antigen; wherein the antibody display system comprises:
(a) an isolated eukaryotic host cell (e.g., *Pichia* such as *Pichia pastoris*) comprising one or more polynucleotides encoding an immunoglobulin light chain; and one or more polynucleotides encoding an immunoglobulin heavy chain that complexes with the light immunoglobulin chain or a functional fragment thereof of a bait; and
(b) a bait comprising a light immunoglobulin chain or functional fragment thereof fused to a surface anchor polypeptide or functional fragment thereof (e.g., SED1);
and determining if a bait/antigen-binding fragment or bait/antibody comprising said bait and heavy and light chain immunoglobulins specifically binds, at the cell surface, to said antigen;
wherein the secreted antibody or antigen-binding fragment thereof is determined to specifically bind said antigen if said bait/antigen-binding fragment or bait/antibody specifically binds, at the cell surface, to said antigen.

In an embodiment of the invention, the method further comprises isolating the identified polynucleotides. In an embodiment of the invention, the method further comprises inhibiting expression of said bait, and determining the affinity of said secreted antibody or antigen-binding fragment thereof for said antigen.

In yet an additional embodiment of the invention, the method further comprises recombinantly expressing the immunoglobulin chains encoded by the polynucleotides and, optionally, isolating an antibody or antigen-binding fragment thereof comprising said immunoglobulins and, optionally, producing a pharmaceutical formulation comprising combining said antibody or antigen-binding fragment thereof and a pharmaceutically acceptable carrier.

The present invention also provides a method for making an antibody display system comprising:
(a) providing an isolated eukaryotic host cell (e.g., *Pichia* such as *Pichia pastoris*),
(b) introducing, into said host cell a bait comprising a light chain immunoglobulin domain fused to a surface anchor polypeptide; and
  (i) one or more polynucleotides encoding an immunoglobulin light chain; and
  (ii) one or more polynucleotides encoding an immunoglobulin heavy chain.

The present invention also provides an antibody display system that is a product of the methods described herein.

The present invention also provides an antibody display system that utilizes any glycoengineered *Pichia* that is capable of producing heterologous proteins with human like N-glycans, as a host.

The present invention also provides a method for making an antibody or antigen-binding fragment thereof comprising introducing, into an isolated eukaryotic host cell (e.g., *Pichia* such as *Pichia pastoris*) comprising a bait that comprises a light chain immunoglobulin or functional fragment thereof fused to a surface anchor polypeptide or functional fragment thereof, one or more polynucleotides encoding an immunoglobulin light chain; and/or one or more polynucleotides encoding an immunoglobulin heavy chain; and culturing the host cell under condition whereby the polynucleotides encoding the immunoglobulin chains are expressed and an antibody or antigen-binding fragment thereof is formed from said chains; wherein said bait is operably associated with a regulatable promoter and bait expression is inhibited when said immunoglobulin chains are expressed.

The present invention also provides a method for determining the effect of a sugar on an antibody or antigen-binding fragment thereof which specifically binds to an antigen comprising contacting an antibody display system with said antigen; wherein the antibody display system comprises:
(a) an isolated controlled glycosylation eukaryotic host cell (e.g., *Pichia* such as *Pichia pastoris*) comprising a polynucleotide encoding an immunoglobulin light chain; and a polynucleotide encoding an immunoglobulin heavy chain; and
(b) a bait comprising a light chain immunoglobulin or functional fragment thereof fused to a surface anchor polypeptide or functional fragment thereof (e.g., SED1) on the surface of said host cell;
wherein the light chain immunoglobulin of said bait complexes with said immunoglobulin heavy chain and immunoglobulin light chain on the surface of the host cell; wherein said heavy or light chain comprises said sugar;
determining if said bait/antigen-binding fragment specifically binds to said antigen;
determining the binding affinity of the antibody or antigen-binding fragment thereof comprising said sugar for the antigen; and
comparing the affinity of the antibody or antigen-binding fragment thereof with affinity of an otherwise identical antibody or antigen-binding fragment thereof which lacks said sugar;
wherein the sugar is determined to increase affinity for the antigen if the affinity of the antibody or antigen-binding fragment thereof comprising said sugar is higher than the affinity of the antibody or antigen-binding fragment thereof which lacks the sugar, and/or wherein the sugar is determined to decrease affinity for the antigen if the affinity of antibody or antigen-binding fragment thereof comprising said sugar is lower than the affinity of the antibody or antigen-binding fragment thereof which lacks the sugar.

The present invention also provides a method for determining the whether an mutation in an immunoglobulin heavy chain Fc region increases or decreases binding of said chain to an Fc receptor (e.g., FcγRI (CD64), FcγRIIA (CD32), FcγRIIB (CD32), FcγRIIIA (CD16a), FcγRIIIB (CD16b).) or to a lectin (e.g., DC-SIGN (CD209) and mouse ortholog SIGN-R, DCIR (dendritic cells inhibitory receptor)) comprising contacting an antibody display system with said Fc receptor or lectin; wherein the antibody display system comprises: (a) an isolated eukaryotic host cell (e.g., *Pichia* such as *Pichia pastoris*) comprising a polynucleotide encoding an immunoglobulin light chain; and a polynucleotide encoding an immunoglobulin heavy chain which comprises the mutation(s); and (b) a bait comprising a light chain immunoglobulin or functional fragment thereof fused to a surface anchor polypeptide (e.g., SED1) or functional fragment thereof on the surface of said eukaryotic host cell; wherein the light chain immunoglobulin of said bait complexes with the heavy chain immunoglobulin, to form a bait/antigen-binding fragment or bait/antibody complex, on the surface of the host cell; and determining if said bait/antigen-binding fragment or bait/antibody specifically binds to said Fc receptor or lectin; and determining the binding affinity of the antibody or antigen-binding fragment thereof for the Fc receptor or lectin; and comparing the affinity of the antibody or antigen-binding fragment thereof with affinity of an otherwise identical antibody or antigen-binding fragment thereof which lacks said mutation; wherein the mutation is determined to increase affinity of the heavy chain for the Fc receptor or lectin if the affinity of the antibody or antigen-binding fragment thereof comprising said mutation is higher than the affinity of the antibody or antigen-binding fragment thereof which lacks the mutation, and/or wherein the mutation is determined to decrease affinity for the Fc receptor or lectin if the affinity of antibody or antigen-binding fragment thereof comprising said mutation is lower than the affinity of the antibody or antigen-binding fragment thereof which lacks the mutation.

BRIEF DESCRIPTION OF THE FIGURES

FIG. 3A shows parental anti-Her2 strain without Lc-Sed1p bait. FIG. 3B shows an anti Her2 IgG1 strain containing the Lc-Sed1p bait. FIG. 3C shows Lc-Sed1p co-expressed with anti-PCSK9 IgG2 that harbors a mutation in the Fc region (F243A/V264A). FIG. 3D shows Lc-Sed1p co-expressed with anti-PCSK9 IgG2 that harbors a mutation in the Fc region F243A/V264A/S267E/L328F.

DETAILED DESCRIPTION OF THE INVENTION

The present invention provides a method and system for antibody surface display that simultaneously features a display mode and full antibody secretion mode. Host cells secrete full antibody or antigen-binding fragment thereof (e.g., Fab, Fab', F(ab')$_2$ or single chain antibody) and display bait/antigen-binding fragments or bait/antibodies on the cell surface. This method utilizes a light immunoglobulin chain (e.g., VL-CL; e.g., human) fusion (e.g., fused at the N- or C-terminus) with a cell surface protein, such as SED-1, as "bait" that is covalently coupled to the cell surface (e.g., the cell wall), on, or embedded (partially or fully) in the cell membrane (e.g., as a transmembrane protein) and that is co-expressed with immunoglobulin chains of an antibody or antigen-binding fragment thereof (e.g., a single specific antibody or fragment from a clonal source or from a library). In an embodiment of the invention, in the endoplasmic reticulum, where antibody molecules normally dimerize to form a full antibody molecule, the light chain immunoglobulin of the bait heterodimerizes with a heavy chain of said antibody or antigen-binding fragment thereof (e.g., forming a monovalent antibody fragment) which complex is displayed on the cell surface. Light/heavy chain complexes, such as monovalent antibody fragments, on the cell surface, can bind antigen.

Figure 1:
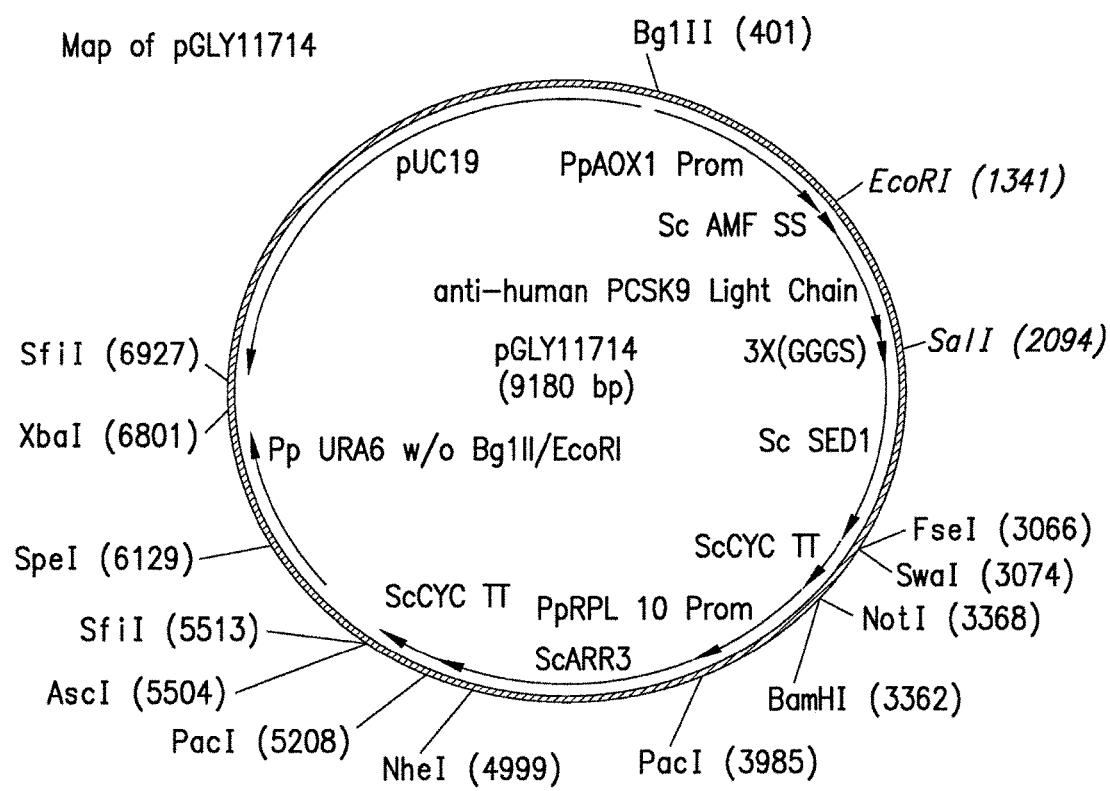
FIG. 1: Plasmid map of pGLY11714 containing anti-PCSK9 Lc bait cassette.
Figure 2:
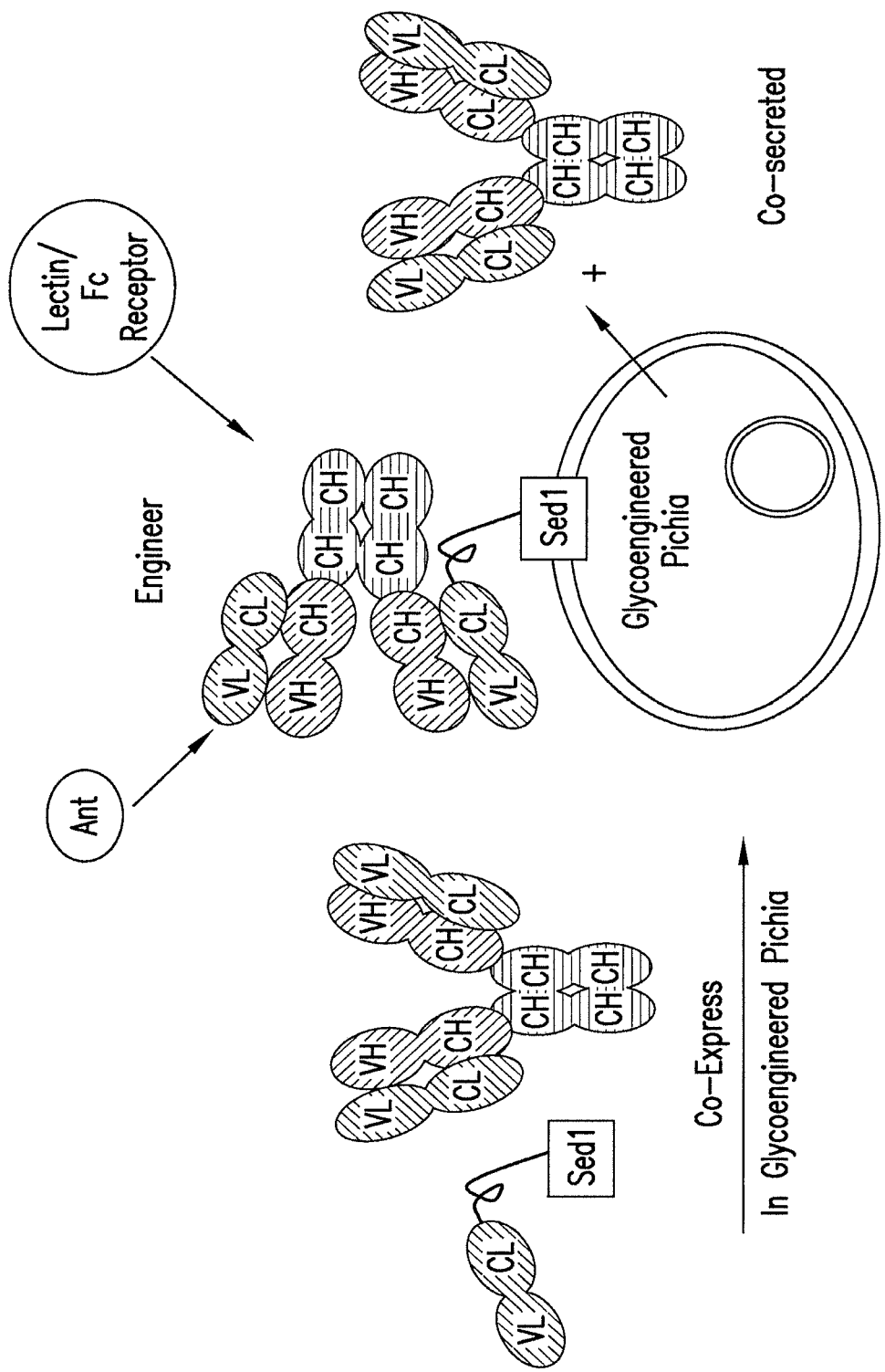
FIG. 2: A schematic representation of the Lc-Sed1p antibody display system. The DNA sequence comprising the IgG light chain (Lc) is fused through a flexible linker to a cell wall anchoring partner, in this case the S. cerevisiae GPI anchor Sed1p is used. When co-expressed in the same host with a secretable full length IgG molecule, the Lc portion of the anchored fusion (the bait) heterodimerizes in the ER with the heavy chain (Hc) region of the IgG molecule, forming disulfide bridges. Since the surface displayed half IgG molecule can still pair with secreted heavy and light chains (H+L), this complex results in surface display of the full length IgG molecule (two heavy chains paired with two light chains, i.e., H2+L2). Meanwhile the assembly of soluble full length IgG occurs with equal probability resulting in secretion of the bivalent (H2+L2) in the culture medium.

While not wishing to be bound by theory, embodiments of the present invention operate by surface displaying an antibody light chain and utilizing the covalent interaction of this light chain with the heavy chain of an antibody molecule that is co-expressed in the same host. This interaction tethers the IgG molecule on the cell surface (See FIG. 2). This display allows for the discovery of novel Fc variants that possess specific desired biological properties, such as Fc receptor binding affinities. It also allows for engineering of the Fab region. Previous methods relied on capturing antibodies on the cell surface following secretion in culture medium. Methods and capture systems of the present invention avoid cross-contamination between clones within the same culture by capturing the antibody prior to secretion. Advantageously, embodiments of the present invention allow co-secretion of the displayed molecule allowing further in vitro analysis.

A complex between the bait (e.g., the light chain immunoglobulin of the bait) and a heavy chain immunoglobulin may be referred to as a "bait/antigen-binding fragment".

In an embodiment of the invention, the antibody display system of the present invention and methods of making or using such a system specifically excludes embodiments wherein the bait comprises any heavy immunoglobulin chains or fragments thereof that are fused to the cell surface protein, e.g., Hc-Sed1p.

The antibody system of the present invention can be employed in any host cell (e.g., yeast, mammalian cells, bacteria) wherein a bait can be expressed at the host cell surface and, for example, wherein the bait/antigen-binding fragment or bait/antibody can bind to an antigen while on the cell surface.

In an embodiment of the invention, formation of antibody or antigen-binding fragment thereof, free of bait, still occurs allowing secretion of the antibody or fragment into the culture supernatant. The secreted antibody or fragment can be used, e.g., for preclinical studies, e.g., after isolation.

If desired, bait can be knocked-out or mutated or its expression can be turned off to create a strain producing only the antibody or fragment (free of bait).

Molecular Biology

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook, et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* (B. D. Hames & S. J. Higgins eds. (1985)); *Transcription And Translation* (B. D. Hames & S. J. Higgins, eds. (1984)); *Animal Cell Culture* (R. I. Freshney, ed. (1986)); *Immobilized Cells And Enzymes* (IRL Press, (1986)); B. Perbal, *A Practical Guide To Molecular Cloning*

(1984); F. M. Ausubel, et al. (eds.), *Current Protocols in Molecular Biology*, John Wiley & Sons, Inc. (1994).

A library is, in general, a collection of related but diverse polynucleotides that are, in general, in a common vector backbone. For example, a light chain or heavy chain immunoglobulin library may contain polynucleotides, in a common vector backbone, that encode light and/or heavy chain immunoglobulins which are diverse but related in their nucleotide sequence; for example, which immunoglobulins are functionally diverse in their abilities to form complexes with other immunoglobulins, e.g., in an antibody display system of the present invention, and bind a particular antigen. For example, the polynucleotide inserts in the common vector backbone may differ by only one or two or several nucleotides, exhibiting, e.g., 90% or more sequence identity (e.g., 95 or 99%). The library may encode immunoglobulins that form full antibodies or antigen-binding fragments thereof (e.g., Fab, Fab', F(ab')$_2$ or single chain antibody).

A coding sequence is "under the control of", "functionally associated with" or "operably associated with" transcriptional and/or translational control sequences in a cell when the sequences direct RNA polymerase mediated transcription of the coding sequence into RNA, preferably mRNA, which then may be spliced (if it contains introns) and translated into a protein encoded by the coding sequence. Thus, a polynucleotide encoding the bait can be operably associated with a promoter, such as a regulatable promoter or a constitutive promoter.

Polynucleotides discussed herein form part of the present invention. A "polynucleotide", "nucleic acid" or "nucleic acid molecule" includes DNA and RNA, single or double stranded.

Polynucleotides e.g., encoding an immunoglobulin chain or component of the antibody display system of the present invention (e.g., a bait), may, in an embodiment of the invention, be flanked by natural regulatory (expression control) sequences, or may be associated with heterologous sequences, including, e.g., promoters, internal ribosome entry sites (IRES) and other ribosome binding site sequences, enhancers, response elements, suppressors, signal sequences, polyadenylation sequences, introns, 5'- and 3'-non-coding regions, and the like.

Polynucleotides e.g., encoding an immunoglobulin chain or component of the antibody display system of the present invention, may be operably associated with a promoter. A "promoter" or "promoter sequence" is, in an embodiment of the invention, a DNA regulatory region capable of binding an RNA polymerase in a cell (e.g., directly or through other promoter-bound proteins or substances) and initiating transcription of a coding sequence. A promoter sequence is, in general, bounded at its 3' terminus by the transcription initiation site and extends upstream (5' direction) to include the minimum number of bases or elements necessary to initiate transcription at any level. Within the promoter sequence may be found a transcription initiation site (conveniently defined, for example, by mapping with nuclease S1), as well as protein binding domains (consensus sequences) responsible for the binding of RNA polymerase. The promoter may be operably associated with other expression control sequences, including enhancer and repressor sequences or with a nucleic acid of the invention. Promoters which may be used to control gene expression include, but are not limited to, cytomegalovirus (CMV) promoter (U.S. Pat. Nos. 5,385,839 and 5,168,062), the SV40 early promoter region (Benoist, et al., (1981) Nature 290:304-310), the promoter contained in the 3' long terminal repeat of Rous sarcoma virus (Yamamoto, et al., (1980) Cell 22:787-797), the herpes thymidine kinase promoter (Wagner, et al., (1981) Proc. Natl. Acad. Sci. USA 78:1441-1445), the regulatory sequences of the metallothionein gene (Brinster, et al., (1982) Nature 296:39-42); prokaryotic expression vectors such as the □-lactamase promoter (Villa-Komaroff, et al., (1978) Proc. Natl. Acad. Sci. USA 75:3727-3731), or the tac promoter (DeBoer, et al., (1983) Proc. Natl. Acad. Sci. USA 80:21-25); see also "Useful proteins from recombinant bacteria" in Scientific American (1980) 242:74-94; and promoter elements from yeast or other fungi such as the Gal 4 promoter, the ADC (alcohol dehydrogenase) promoter, PGK (phosphoglycerol kinase) promoter or the alkaline phosphatase promoter.

The terms "vector", "cloning vector" and "expression vector" include a vehicle (e.g., a plasmid) by which a DNA or RNA sequence can be introduced into a host cell, so as to transform the host and, optionally, promote expression and/or replication of the introduced sequence. Polynucleotides encoding an immunoglobulin chain or component of the antibody display system of the present invention (e.g., a bait) may, in an embodiment of the invention, be in a vector.

A host cell that may be used in a composition or method of the present invention, as is discussed herein, includes eukaryotes such as lower and higher eukaryotic cells as well as prokaryotes. Higher eukaryote cells include mammalian, insect (e.g., *Spodoptera frugiperda* cells), and plant cells (e.g., Protalix cells). In an embodiment of the invention, the host cell is a lower eukaryote such as a yeast or filamentous fungi cell, which, for example, is selected from the group consisting of any *Pichia* cell, *Pichia pastoris, Pichia finlandica, Pichia trehalophila, Pichia koclamae, Pichia membranaefaciens, Pichia minuta (Ogataea minuta, Pichia lindneri), Pichia opuntiae, Pichia thermotolerans, Pichia salictaria, Pichia guercuum, Pichia pijperi, Pichia stiptis, Pichia methanolica, Pichia, Saccharomyces cerevisiae, Saccharomyces, Hansβnula polymorpha, Kluyveromyces, Kluyveromyces lactis, Candida albicans, Aspergillus nidulans, Aspergillus niger, Aspergillus oryzae, Trichoderma reesei, Chrysosporium lucknowense, Fusarium, Fusaηum gramineum, Fusarium venenatum* and *Neuraspora crassa*. A higher eukaryotic host cell includes a mammalian host cell for example a Chinese hamster ovary (CHO) cell, a BHK cell, or an NSO cell. A prokaryotic host cell can be, for example, a bacterial cell such as *Escherichia* (e.g., *E. coli*), *Enterobacter, Azotobacter, Erwinia, Bacillus, Pseudomonas, Klebsiella, Proteus, Salmonella, Serratia, Shigella, Rhizobia, Vitreoscilla*, and *Paracoccus*. *E. coli* host cells include DHB4, BL21 (which are deficient in both Lon (Phillips et al. (1984) J. Bacteriol. 159: 283) and OmpT proteases), HB101, BL21 DE3, *E. coli* AD494, *E. coli* W3110 (ATCC 27,325), *E. coli* 294 (ATCC 31,446), *E. coli* B, and *E. coli* X1776 (ATCC 31,537). Other strains include *E. coli* B834 which are methionine deficient (Leahy et al. (1992) Science 258, 987); other strains include the BLR strain, and the K-12 strains HMS174 and NovaBlue, which are recA-derivative that improve plasmid monomer yields and may help stabilize target plasmids containing repetitive sequences (these strains can be obtained from Novagen). See also U.S. Pat. Nos. 4,952,496, 5,693,489 and 5,869,320 and in Davanloo, P., et al., (1984) Proc. Natl. Acad. Sci. USA 81, 2035-2039; Studier, F. W., et al., (1986) J. Mol. Biol. 189: 113-130; Rosenberg, A. H., et al., (1987) Gene 56: 125-135; and Dunn, J. J., et al., (1988) Gene 68: 259. Prokaryotic cells can also be cultured, for example, in a medium under conditions allowing for recombinant expression of a polypeptide, such as an immunoglobulin polypeptide and/or a bait. Such methods and host cells comprising such genes and proteins are part of the present invention. A prokaryotic host cell can also be used as a host cell in the antibody display system of the present invention, as discussed herein.

As used herein, the terms "N-glycan" and "glycoform" are used interchangeably and refer to an N-linked oligosaccharide, e.g., one that is attached by an asparagine-N-acetylglucosamine linkage to an asparagine residue of a polypeptide. N-linked glycoproteins contain an N-acetylglucosamine residue linked to the amide nitrogen of an asparagine residue in the protein. Predominant sugars found on glycoproteins are glucose, galactose, mannose, fucose, N-acetylgalactosamine (GalNAc), N-acetylglucosamine (GlcNAc) and sialic acid (e.g., N-acetyl-neuraminic acid (NANA)).

N-glycans have a common pentasaccharide core of $Man_3GlcNAc_2$ ("Man" refers to mannose; "Glc" refers to glucose; and "NAc" refers to N-acetyl; GlcNAc refers to N-acetylglucosamine). N-glycans differ with respect to the number of branches (antennae) comprising peripheral sugars (e.g., GlcNAc, galactose, fucose and sialic acid) that are added to the $Man_3GlcNAc_2$ ("$Man_3$") core structure which is also referred to as the "triammnose core", the "pentasaccharide core" or the "paucimannose core". N-glycans are classified according to their branched constituents (e.g., high mannose, complex or hybrid). A "high mannose" type N-glycan has five or more mannose residues. A "complex" type N-glycan typically has at least one GlcNAc attached to the 1,3 mannose arm and at least one GlcNAc attached to the 1,6 mannose arm of a "trimannose" core. Complex N-glycans may also have galactose ("Gal") or N-acetylgalactosamine ("GalNAc") residues that are optionally modified with sialic acid or derivatives (e.g., "NANA" or "NeuAc", where "Neu" refers to neuraminic acid and "Ac" refers to acetyl). Complex N-glycans may also have intrachain substitutions comprising "bisecting" GlcNAc and core fucose ("Fuc"). Complex N-glycans may also have multiple antennae on the "trimannose core," often referred to as "multiple antennary glycans." A "hybrid" N-glycan has at least one GlcNAc on the terminal of the 1,3 mannose arm of the trimannose core and zero or more mannoses on the 1,6 mannose arm of the trimannose core. The various N-glycans are also referred to as "glycoforms." "PNGase", or "glycanase" or "glucosidase" refer to peptide N-glycosidase F (EC 3.2.2.18).

In an embodiment of the invention, O-glycosylation of glycoproteins in a "eukaryotic host cell" is controlled. The scope of the present invention includes isolated eukaryotic host cells (e.g., Pichia pastoris) wherein O-glycosylation is controlled (as discussed herein) as well as antibody display systems comprising such eukaryotic host cells and methods of use thereof (as discussed herein). For example, wherein O-glycan occupancy and mannose chain length are reduced. In lower eukaryote host cells such as yeast, O-glycosylation can be controlled by deleting the genes encoding one or more protein O-mannosyltransferases (Dol-PMan: Protein (Ser/Thr) Mannosyl Transferase genes) (PMTs) or by growing the host in a medium containing one or more Pmtp inhibitors. Thus, the present invention includes isolated eukaryotic host cells, antibody display systems and methods of use thereof (as is discussed herein), e.g., comprising a deletion of one or more of the genes encoding PMTs, and/or, e.g., wherein the host cell can be cultivated in a medium that includes one or more Pmtp inhibitors. Pmtp inhibitors include but are not limited to a benzylidene thiazolidinedione. Examples of benzylidene thiazolidinediones are 5-[[3,4bis(phenylmethoxy)phenyl]methylene]-4-oxo-2-thioxo-3-thiazolidineacetic Acid; 5-[[3-(1-25 Phenylethoxy)-4-(2-phenylethoxy)]phenyl]methylene]-4-oxo-2-thioxo-3-thiazolidineacetic Acid; and 5-[[3-(1-Phenyl-2-hydroxy)ethoxy)-4-(2-phenylethoxy)]phenyl]methylene]-4-oxo-2-thioxo3-thiazolidineacetic acid.

In an embodiment of the invention, a "eukaryotic host cell" includes a nucleic acid that encodes an alpha-1,2-mannosidase that has a signal peptide that directs it for secretion. For example, in an embodiment of the invention, the host cell is engineered to express an exogenous alpha-1,2-mannosidase enzyme having an optimal pH between 5.1 and 8.0, preferably between 5.9 and 7.5. In an embodiment of the invention, the exogenous enzyme is targeted to the endoplasmic reticulum or Golgi apparatus of the host cell, where it trims N-glycans such as $Man_8GlcNAc_2$ to yield $Man_5GlcNAc_2$. See U.S. Pat. No. 7,029,872.

"Eukaryotic host cells" are, in an embodiment of the invention, lower eukaryote cells (e.g., yeast such as Pichia pastoris) that are genetically engineered to eliminate glycoproteins having alpha-mannosidase-resistant N-glycans by deleting or disrupting one or more of the beta-mannosyltransferasegenes (e.g., BMT1, BMT2, BMT3, and BMT4) (See, U.S. Published Patent Application No. 2006/0211085) or abrogating translation of RNAs encoding one or more of the beta-mannosyltransferases using interfering RNA, antisense RNA, or the like. The scope of the present invention includes such an isolated eukaryotic host cell (e.g., Pichia pastoris) as well as antibody display systems comprising such eukaryotic host cells and methods of use thereof (as discussed herein).

"Eukaryotic host cells" also include lower eukaryote cells (e.g., yeast and filamentous fungi such as Pichia pastoris) that are genetically engineered to eliminate glycoproteins having phosphomannose residues, e.g., by deleting or disrupting one or both of the phosphomannosyl transferase genes PNO1 and MNN4B (See for example, U.S. Pat. Nos. 7,198,921 and 7,259,007), which can include deleting or disrupting the MNN4A gene or abrogating translation of RNAs encoding one or more of the phosphomannosyltransferases using interfering RNA, antisense RNA, or the like. In an embodiment of the invention, a "eukaryotic host cell" has been genetically modified to produce glycoproteins that have predominantly an N-glycan selected from the group consisting of complex N-glycans (sialylated α2,3 or α2,6 linkages; or asialylated), hybrid N-glycans, and high mannose N-glycans wherein complex N-glycans are, in an embodiment of the invention, selected from the group consisting of $Man_3GlcNAc_2$, $GlcNAc_{(1-4)}Man_3GlcNAc_2$, $Gal_{(1-4)}GlcNAc_{(1-4)}Man_3GlcNAc_2$, and $NANA_{(1-4)}Gal_{(1-4)}Man_3GlcNAc_2$; $NAGNA_{(1-4)}Gal_{(1-4)}Man_3GlcNAc_2$; hybrid N-glycans are, in an embodiment of the invention, selected from the group consisting of $Man_5GlcNAc_2$, $GlcNAcMan_5GlcNAc_2$, $GalGlcNAcMan_5GlcNAc_2$, and $NANAGalGlcNAcMan_5GlcNAc_2$; $NAGNAGalGlcNAcMan_5GlcNAc_2$ and high mannose N-glycans are, in an embodiment of the invention, selected from the group consisting of $Man_6GlcNAc_2$, $Man_7GlcNAc_2$, $Man_81cNAc_2$, and $Man_9GlcNAc_2$. The scope of the present invention includes such an isolated eukaryotic host cell (e.g., Pichia pastoris) as well as antibody display systems comprising such eukaryotic host cells and methods of use thereof (as discussed herein).

As used herein, the term "essentially free of" as it relates to lack of a particular sugar residue, such as fucose, or galactose or the like, on a glycoprotein, is used to indicate that the glycoprotein composition is substantially devoid of N-glycans which contain such residues. Expressed in terms of purity, essentially free means that the amount of N-glycan structures containing such sugar residues does not exceed 10%, and preferably is below 5%, more preferably below 1%, most preferably below 0.5%, wherein the percentages are by weight or by mole percent.

As used herein, a glycoprotein composition "lacks" or "is lacking" a particular sugar residue, such as fucose or galactose, when no detectable amount of such sugar residue is present on the N-glycan structures. For example, in preferred embodiments of the present invention, the glycoprotein compositions are produced by lower eukaryotic organisms, as discussed herein, and will "lack fucose," because the cells of these organisms do not have the enzymes needed to produce fucosylated N-glycan structures. Thus, the term "essentially free of fucose" encompasses the term "lacking fucose." However, a composition may be "essentially free of fucose" even if the composition at one time contained fucosylated N-glycan structures or contains limited, but detectable amounts of fucosylated N-glycan structures as described above.

For example, a host cell which introduces, eliminates or modifies sugar residues on an immunoglobulin expressed in the host cell, e.g., as is discussed herein, may, in certain instances, be referred to herein as a "controlled glycosylation host cell."

The scope of the present invention includes isolated eukaryotic host cells (e.g., *Pichia pastoris*), e.g., any of those discussed herein, comprising an antibody display system of the present invention or any component thereof (e.g., a bait and/or polynucleotide(s) encoding a bait; and/or an immunoglobulin chain and/or polynucleotide(s) encoding the immunoglobulin chain); as well as antibody display systems comprising such eukaryotic host cells and methods of use thereof (as discussed herein).

Fluorescence-activated cell sorting (FACS) is a specialized type of flow cytometry. It provides a method for sorting a heterogeneous mixture of biological cells into two or more containers, one cell at a time, based upon the specific light scattering and fluorescent characteristics of each cell. The present invention encompasses methods of using the antibody display system of the present invention, e.g., as discussed herein, wherein the eukaryotic host cells that are bound to an antigen of interest (by the bait/antigen-binding fragment or bait/antibody) are sorted from unbound cells or cells without sufficient levels of binding, by FACS sorting. FACS sorting can, in an embodiment of the invention, be based on whether the cells are labeled with a detectable fluorescent label (e.g., wherein the antigen itself or a secondary antibody is labeled). For example, cells displaying a bait/antibody or bait/antigen-binding fragment that bind an antigen of interest can be identified based on binding of a fluorescently labeled antigen to the bait/antibody or bait/antigen-binding fragment; or based on binding of a fluorescently labeled secondary antibody to the antigen that is bound to the bait/antibody or bait/antigen-binding fragment. Such sorted, labeled host cells and compositions comprising such sorted labeled host cells are also part of the present invention.

A regulatable promoter is a promoter whose expression can be induced or inhibited. Embodiments of the invention include the antibody display system wherein expression of the bait is controlled by a regulatable promoter as well as methods of use thereof as discussed herein. Polynucleotides encoding the bait, operably associated with a regulatable promoter also form part of the present invention along with isolated eukaryotic host cells including the polynucleotides.

Examples of regulatable promoters that occur in yeast include the GUT1 promoter, GADPH promoter and the PCK1 promoter.

In an embodiment of the invention, expression of a polynucleotide (e.g., the bait) in a eukaryotic host cell (e.g., a bait) is inhibited by exposing the cells to anti-sense RNA or by RNA interference (e.g., microRNA (miRNA) or small interfering RNA (siRNA)). Embodiments of the invention include methods of using antibody display system (e.g., as discussed herein) wherein expression of the bait is inhibited by RNA interference or anti-sense RNA. Isolated eukaryotic host cells of the present invention (e.g., as discussed herein) comprising bait and further comprising an anti-sense or RNA interference molecule that inhibits bait expression are part of the present invention.

Fc receptors include, for example, FcγRI (CD64), FcγRIIA (CD32), FcγRIIB (CD32), FcγRIIIA (CD16a), and FcγRIIIB (CD16b); and Lectins include, for example, DC-SIGN (CD209) and mouse ortholog SIGN-R, and DCIR (dendritic cells inhibitory receptor).

Antibodies

Host cells of the present invention include (in addition to the bait) polynucleotides encoding heavy and light immunoglobulins that complex to form an antibody or antigen-binding fragment thereof which may be secreted from the host cell. Heavy chains encoded by a polynucleotide may complex with the light chain immunoglobulin to form a bait/antigen-binding fragment or bait/antibody that includes one or more antigen-binding sites. When on the surface of the cell, the bait/antigen-binding fragment or bait/antibody may bind to an antigen and this binding may be detected, e.g., by FACS, thus indicating that the heavy and light chains comprise binding sites with specificity for the antigen.

Antibodies or antigen-binding fragments thereof identified in connection with use of the present invention (e.g., use of the antibody display system of the present invention) may be reformatted into any suitable form. For example, CDRs from a full antibody isolated using the antibody display system can be incorporated into a different framework (e.g., a human framework) to generate an antibody or antigen-binding fragment comprising the CDRs isolated from the antibody display system of the present invention. Methods for producing chimeric, humanized and human antibodies are well known in the art. See, e.g., U.S. Pat. No. 5,530,101, issued to Queen et al., U.S. Pat. No. 5,225,539, issued to Winter et al., U.S. Pat. No. 4,816,397 issued to Boss et al. Such methods for reformatting an antibody or antigen-binding fragment or for relocating CDRs from one framework to another are conventional and well known in the art. For example, the CDRs of an antibody or antigen-binding fragment can be used to generate monoclonal antibodies, polyclonal antibodies, bispecific antibodies, chimeric antibodies, recombinant antibodies, anti-idiotypic antibodies, humanized antibodies and bispecific antibodies; or antigen-binding fragments thereof such as nanobodies, Fab, Fab', F(ab')$_2$, Fv fragments; dsFv; (dsFv)$_2$, ds diabodies; dsFv-dsFv'; single-chain antibody molecules, e.g., sc-Fv, sc-Fv dimers (bivalent diabodies); and bispecific diabodies.

A full antibody comprises a tetramer of subunits. Each tetramer has two identical pairs of polypeptide chains, each pair having one "light" chain (LC) and one "heavy" chain (HC). Light chains (LCs) are classified as either kappa or lambda based on the type of constant domain in the light chain. Heavy chains (HCs) are classified as gamma, mu, alpha, delta, or epsilon, based on the type of constant domain in the heavy chain, and define the antibody's isotype as IgG (e.g., IgG1, IgG2, IgG2a, IgG2b, IgG3 or IgG4), IgM, IgA (e.g., IgA1 or IgA2), IgD or IgE, respectively.

The present invention encompasses methods for making an antibody or antigen-binding fragment thereof comprising introducing, into an isolated host cell (e.g., a eukaryotic host cell such as *Pichia*, e.g., *Pichia pastoris*) comprising a bait comprising a light immunoglobulin chain (e.g., VL-CL; e.g., human) fused to a surface anchor, e.g., SED-1, or a functional fragment thereof; one or more polynucleotides encoding an immunoglobulin light chain; and/or one or more polynucleotides encoding an immunoglobulin heavy chain and culturing the host cell under condition whereby the polynucleotides encoding the immunoglobulin light and heavy chains are expressed and an antibody or antigen-binding fragment thereof is formed from said chains.

In an embodiment of the invention, said bait is operably associated with a regulatable promoter and the bait expression is inhibited when said immunoglobulin chains are expressed. In an embodiment of the invention, bait expression is inhibited with anti-sense RNA or by RNA interference.

The present invention also provides a method for determining the quantity of an antibody or antigen-binding fragment thereof, e.g., by enzyme linked immunosorbent assay (ELISA). For example, in an embodiment of the invention, the method comprises culturing a eukaryotic host cell comprising an isolated polypeptide comprising a bait polypeptide comprising a light immunoglobulin chain (e.g., VL-CL; e.g., human) fused to a surface anchor polypeptide or functional fragment thereof); wherein the host cell secretes full antibody or antigen-binding fragment thereof (optionally, the antibody or fragment is isolated from the host cell and/or culture medium); and determining the quantity of the antibody or antigen-binding fragment thereof by ELISA. In an embodiment of the invention, expression of the bait is inhibited before quantitation such that the host cell expresses and secretes only full antibody. Bait polynucleotide can be operably associated with a regulatable promoter which is inhibited so as to inhibit bait expression. For example, in an embodiment of the invention, ELISA comprises coating the antigen on a solid substrate; binding the antibody or antigen-binding fragment thereof to the antigen; binding a detectably labeled secondary antibody to the antibody or fragment; and detecting the secondary antibody. In an embodiment of the invention, the secondary antibody is labeled with alkaline phosphatase or horse radish peroxidase. In an embodiment of the invention, the label is detected by binding the alkaline phosphatase (AP) or horse radish peroxidase (HRP) with substrate and measuring absorbance of the plate (e.g., HRP substrate 3,3',5,5'-tetramethylbenzidine (TMB); HRP substrate 3,3'-diaminobenzidine (DAB); or HRP substrate 2,2'-azino-bis(3-ethylbenzthiazoline-6-sulphonic acid) (ABTS); or AP substrate para-nitrophenylphosphate).

The present invention also provides a method for determining the affinity of an antibody or antigen-binding fragment thereof, that is secreted from a eukaryotic host cell in the antibody display system of the present invention, for an antigen. For example, the affinity can be determined by standard affinity ELISA, Biacore™ analysis or competition assays.

Antibody Display System

The present invention provides an antibody display system, composition or kit comprising (1) a eukaryotic host cell and (2) a bait comprising a light immunoglobulin chain (e.g., VL-CL; e.g., human) fused, at the N- or C-terminus, optionally, by a peptide linker such as GGGS (×3), to a surface anchor which bait is optionally linked to a signal sequence (e.g., an alpha mating factor signal sequence, e.g., from *Saccharomyces cerevisiae*); which system may be used, for example, in the identification of antibodies and antigen-binding fragments thereof that bind an antigen of interest. Thus, in an embodiment of the invention, the host cell in the system expresses one or more immunoglobulin chains (e.g., light and heavy chains, e.g., wherein one or more of the chains are from a library source) of an antibody or antigen-binding fragment thereof, and/or of a bait/antigen-binding fragment or bait/antibody.

The light chain immunoglobulin of the bait may be the same or different from the light chain immunoglobulin that is not part of the bait. A host cell may contain more than one sequence of heavy chain immunoglobulin.

A bait/antigen-binding fragment of an antibody (1) is a complex between light immunoglobulin chain of the bait (e.g., VL-CL; e.g., human) and a heavy chain immunoglobulin; and, (2) binds to an antigen when on the surface of the host cell. An example of a bait/antigen-binding fragment is a monovalent fragment of a full antibody (i.e., a monovalent antibody fragment) bound to the cell surface anchor of the bait. A bait/antibody is a complex between light immunoglobulin chain of the bait (e.g., VL-CL; e.g., human) and light and heavy chain immunoglobulins which form a full antibody tetrameric complex having two heavy and two light chains; that binds to an antigen when on the surface of the host cell.

A "monovalent antibody fragment" comprises one half of an antibody, i.e., the antibody heavy chain (VH-CH1-CH2-CH3) bound to the antibody light chain (VL-CL) comprising three paired CDRs, e.g., wherein CH1 and CL are bound by a disulfide bridge, which monovalent antibody fragment is capable of detectably binding an antigen.

The "bait" comprises a light chain immunoglobulin such as, for example, a CL polypeptide or a VL-CL polypeptide fused, e.g., at the amino-terminus or carboxy-terminus, to a cell surface anchor, which bait possesses functional properties described herein (e.g., as set forth below) that enable the bait to function in the antibody display system of the present invention. The light chain immunoglobulin of the bait can, in an embodiment of the invention, be mutated so as to improve its ability to function in the antibody display system of the present invention, for example, cysteines or other residues may be added or moved to allow for more extensive disulfide bridges to form when complexed with a heavy chain immunoglobulin. A light chain immunoglobulin suitable for use in the bait is capable of dimerizing, when fused to a surface anchor protein, with, for example, a heavy chain immunoglobulin; on the surface of a eukaryotic host cell. In an embodiment of the invention, dimerization between the bait and immunoglobulin heavy chain occurs intracellularly, prior to routing to the cell surface, wherein heavy chain immunoglobulin and the bait remain associated once at the cell surface. In an embodiment of the invention, a full antibody or antigen-binding fragment thereof that is co-expressed with the bait comprises light and heavy chains capable of dimerizing with each other to form a monovalent antibody fragment, which monovalent antibody fragment is also capable of dimerizing with a complex between the light chain of the bait and a heavy chain immunoglobulin. (See FIG. 2).

An antigen can be any immunogenic molecule or substance, for example, a polypeptide (e.g., an oligopeptide), a cell membrane, cell extract or a whole cell. Polypeptide antigens include, for example, the following polypeptides: chemokines, cytokines (e.g., inflammatory cytokines or chemokines), receptors, PCSK9, granulocyte-CSF; coagulation factors such as factor VIII, factor IX, and human protein C; soluble IgE receptor alpha-chain; urokinase; chymase and urea trypsin inhibitor; IGF-binding protein; insulin-like growth factor-1 receptor, vascular epidermal growth factor, epidermal growth factor; growth hormone-releasing factor; GITR (glucocorticoid-induced TNFR-related protein), annexin V fusion protein; IL-23p19, IL-23p40, IL-23R, IL12R-beta 1, TNF alpha (tumor necrosis factor alpha), TGF beta (transforming growth factor beta), IL-10, IL-17, TSLP (Thymic stromal lymphopoietin), angiostatin; vascular endothelial growth factor-2; myeloid progenitor inhibitory factor-1; osteoprotegerin (OPG), RANK (receptor activator for nuclear factor kappa B) or RANKL (receptor activator for nuclear factor kappa B ligand); any of which can be, in an embodiment of the invention, human.

A "surface anchor" is any polypeptide that, when fused with a light chain immunoglobulin or functional fragment thereof (e.g., VL-CL or CL or VL), is expressed and located to the cell surface and to which a heavy chain immunoglobulin can complex via binding to the light chain immunoglobulin of the bait. Examples of a suitable cell surface anchor is a protein such as, but not limited to any of the following: SED1P, α-agglutinin, Cwp1, Cwp2, GasI, Yap3, FloIp1 Crh2, Pir1, Pir4, Tip1, Wpi, Hpwpl, Als3, and Rbt5; for example, *Saccharomyces cerevisiae* CWP1, CWP2, SED1, or GAS1; *Pichia pastoris* SP1 or GAS1; or *H. polymorpha* TIP1; or any functional fragment or variant thereof these proteins, which are described in international publication No. WO09/111183. In an embodiment of the invention, the surface anchor is any glycosylphosphatidylinositol-anchored (GPI) protein. A functional fragment of a surface anchor comprises a fragment of a full surface anchor polypeptide that can, to some degree, function, as does a full surface anchor polypeptide, in the antibody display system of the present invention.

As discussed herein, a suitable eukaryotic host cell for use in the antibody display system of the present invention is a *Pichia* cell such as *Pichia pastoris*.

The scope of the present invention encompasses an isolated eukaryotic host cell (e.g., *Pichia pastoris*) comprising a bait, e.g., on the cell surface, optionally, wherein the bait is dimerized with one or more immunoglobulin chains to form a bait/antigen-binding fragment or bait/antibody. The present invention also includes a composition comprising such a eukaryotic host cell further comprising a secreted antibody or antigen-binding fragment thereof, e.g., in a liquid culture medium.

The present invention provides, for example, methods for using the antibody display system of the present invention. For example, the present invention comprises a method for identifying (i) an antibody or antigen-binding fragment thereof; or, a bait/antigen-binding fragment or bait/antibody, that binds specifically to an antigen of interest; and/or (ii) a polynucleotide encoding an immunoglobulin heavy or light polypeptide chain of any of the foregoing; or either of said immunoglobulin polypeptide chains themselves. The method comprises, in an embodiment of the invention:

(a) co-expressing a bait (e.g., comprising a polypeptide comprising light chain immunoglobulin that is linked to a cell surface anchor, such as Sed1p) and one or more heavy and light immunoglobulin chains (e.g., wherein one or more of such chains are encoded by a polynucleotide from a library source) in an isolated eukaryotic host cell (e.g., *Pichia pastoris*) such that a complex between the light chain immunoglobulin of the bait and one or more of said heavy chain immunoglobulins forms (e.g., a bait/antibody or bait-antigen-binding fragment), and is located at the cell surface; for example, wherein the host cell is transformed with one or more polynucleotides encoding the bait and/or the immunoglobulin chains;

(b) identifying a eukaryotic host cell expressing the bait, dimerized with the heavy chain immunoglobulin, which has detectable affinity (e.g., acceptable affinity) for the antigen (e.g., which detectably binds to the antigen);

In an embodiment of the invention, non-tethered, secreted full antibodies or antigen-binding fragments thereof comprising light and heavy chain immunoglobulins that were introduced into the host cell are formed. These may be analyzed to determine if they possess detectable affinity.

In an embodiment of the invention, the full antibodies or antigen-binding fragments thereof are secreted from the host cell into the medium. In an embodiment of the invention, the secreted full antibodies or antigen-binding fragments thereof are isolated from the host cell and/or medium.

In an embodiment of the invention, after step (b), expression of the bait in the host cell is inhibited, but expression of the full antibodies or antigen-binding fragments thereof is not inhibited. In this embodiment of the invention, the host cell expresses only the full antibody but does not express the bait at any significant quantity. Once expression of the bait is inhibited, in an embodiment of the invention, the full antibody produced from the host cell is analyzed to determine if it possesses detectable affinity (e.g., acceptable affinity); and, (c) identifying said antibodies or antigen-binding fragments or polynucleotides if detectable binding of the bait/antigen-binding fragment or bait/antibody to antigen is observed, e.g., wherein one or more of the polynucleotides encoding the light and/or heavy chain immunoglobulin are optionally isolated from the host cell. In an embodiment of the invention, the nucleotide sequence of the polynucleotide is determined.

In an embodiment of the invention, a population of host cells express a common bait and a common immunoglobulin heavy chain as well a variety of different light chain immunoglobulins (non-bait chains), e.g., from a library source, wherein individual light chain immunoglobulins that form bait/antigen-binding fragments and full antibodies that are tethered to the bait and which exhibit antigen binding can be identified. Similarly, in an embodiment of the invention, a population of host cells express a common bait and a common immunoglobulin light chain (non-bait) as well a variety of different heavy chain immunoglobulins, e.g., from a library source, wherein individual heavy chain immunoglobulins that form bait/antigen-binding fragments and full antibodies that are tethered to the bait and which exhibit antigen binding can be identified.

In an embodiment of the invention, the host cell possessing polynucleotides encoding the heavy and light chain immunoglobulins can be further used to express the secreted non-tethered antibody (e.g., full antibody) or an antigen-binding fragment thereof in culture. For example, in this embodiment of the invention, expression of the bait is optionally inhibited so that bait expression at significant quantities does not occur. The host cell is then cultured in a culture medium under conditions whereby secreted, non-tethered antibody (e.g., full antibody) or antigen-binding fragment thereof is expressed and secreted from the host cell. The non-tethered antibody or antigen-binding fragment thereof can optionally be isolated from the host cell and culture medium. In an embodiment of the invention, the immunoglobulin chains are transferred to a separate host cell (e.g., lacking the antibody display system components) for recombinant expression.

The antibody display system of the present invention may be used to evaluate the effects of a given glycosylation pattern on the affinity of an antibody or antigen-binding fragment thereof for an antigen. In general, the ability of the bait/antigen-binding fragment or bait/antibody comprising an altered glycosylation pattern to bind antigen may be evaluated, after which affinity of free full antibody or antigen-binding fragment thereof can be evaluated. Glycosylation patterns can be modified on the immunoglobulin chains expressed in the antibody display system, for example, by using a host cell, e.g., as is discussed herein, that modifies the glycosylation patterns when the chains are expressed and/or by culturing a host under conditions whereby the glycosylation pattern is modified, e.g., as discussed herein. For example, in an embodiment of the invention, the method comprise contacting an antibody display system with said antigen; wherein the antibody display system comprises: (a) an isolated eukaryotic controlled glycosylation host cell comprising a polynucleotide encoding an immunoglobulin light chain; and a polynucleotide encoding an immunoglobulin heavy chain; and (b) a bait comprising a light chain immunoglobulin or functional fragment thereof fused to a surface anchor polypeptide or functional fragment thereof on the surface of said eukaryotic host cell; wherein the light chain immunoglobulin of said bait complexes with a heavy chain immunoglobulin, to form a bait/antigen-binding fragment or bait/antibody, on the surface of the host cell; wherein said heavy or light chain comprises said sugar; determining if said bait/antigen-binding fragment or bait/antibody specifically binds to said antigen; determining the binding affinity of the antibody or antigen-binding fragment thereof comprising said sugar for the antigen; and comparing the affinity of the antibody or antigen-binding fragment thereof with affinity of an otherwise identical antibody or antigen-binding fragment thereof which lacks said sugar; wherein the sugar is determined to increase affinity for the antigen if the affinity of the antibody or antigen-binding fragment thereof comprising said sugar is higher than the affinity of the antibody or antigen-binding fragment thereof which lacks the sugar, and/or wherein the sugar is determined to decrease affinity for the antigen if the affinity of antibody or antigen-binding fragment thereof comprising said sugar is lower than the affinity of the antibody or antigen-binding fragment thereof which lacks the sugar. For example, the affinity of the antibody or antigen-binding fragment thereof lacking the sugar can be determined in a similar manner in the antibody display system of the present invention or the affinity of it can be determined directly by measuring affinity by a known method such as ELISA, Biacore™ assay or a competition assay.

Bait expression can be inhibited by any of several acceptable means. For example, the polynucleotides encoding the bait can be expressed by a regulatable promoter whose expression can be inhibited in the host cell. In an embodiment of the invention, bait expression is inhibited by RNA interference, anti-sense RNA, mutation or removal of the polynucleotide encoding the bait from the host cell or genetic mutation of the polynucleotide so that the host cell does not express a functional bait.

"Acceptable affinity" refers to antibody or antigen-binding fragment affinity for the antigen which is at least about $10^{-3}$ M or a greater affinity (lower number), e.g., about $10^{-3}$ M, $10^{-4}$ M, $10^{-5}$ M, $10^{-6}$ M, $10^{-7}$ M, $10^{-8}$ M, $10^{-9}$ M, $10^{-10}$ M, $10^{-11}$ M or $10^{-12}$ M.

In an embodiment of the present invention, polynucleotides encoding the free antibody or antigen-binding fragment thereof; or the bait/antigen-binding fragment or bait/antibody heavy and light immunoglobulin chains are in one or more libraries of polynucleotides that encode light and/or heavy chain immunoglobulins (e.g., one library encoding light chains and one library encoding heavy chains). The particular immunoglobulin chains of interest are, in this embodiment, distinguished from the other chains in the library when the surface-anchored bait/antigen-binding fragment or bait/antibody on the host cell surface is observed to bind to an antigen of interest.

In an embodiment of the invention, the heavy or light chain immunoglobulin expressed in the antibody display system is from a library source and the other immunoglobulin chain is known (i.e., a single chain from a clonal source). In this embodiment of the invention, the antibody display system can be used, as discussed herein, to identify a new library chain that forms desirable antibodies or antigen-binding fragments thereof when coupled with the known chain. Alternatively, the antibody display system can be used to analyze expression and binding characteristics of an antibody or antigen-binding fragment thereof comprising two known immunoglobulin chains.

The antibody display system of the present invention may be used to evaluate whether a one or more mutations in an immunoglobulin heavy chain (e.g., the Fc region of the immunoglobulin heavy chain, e.g., in the CH2 and/or CH3 domain of the heavy chain) agonizes or antagonizes binding of the heavy chain to an Fc receptor (e.g., FcγRI (CD64), FcγRIIA (CD32), FcγRIIB (CD32), FcγRIIIA (CD16a), FcγRIIIB (CD16b)) or to a lectin (e.g., DC-SIGN (CD209) and mouse ortholog SIGN-R, DCIR (dendritic cells inhibitory receptor)). For example, in an embodiment of the invention, the method comprise contacting an antibody display system with said Fc receptor or lectin; wherein the antibody display system comprises: (a) an isolated eukaryotic host cell comprising a polynucleotide encoding an immunoglobulin light chain; and a polynucleotide encoding an immunoglobulin heavy chain which comprises the mutation(s) to be evaluated; and (b) a bait comprising a light chain immunoglobulin or functional fragment thereof fused to a surface anchor polypeptide or functional fragment thereof on the surface of said eukaryotic host cell; wherein the light chain immunoglobulin of said bait complexes with a heavy chain immunoglobulin, to form a bait/antigen-binding fragment or bait/antibody, on the surface of the host cell; determining if said bait/antigen-binding fragment or bait/antibody specifically binds to said Fc receptor or lectin; determining the binding affinity of the antibody or antigen-binding fragment thereof for the Fc receptor or lectin; and comparing the affinity of the antibody or antigen-binding fragment thereof with affinity of an otherwise identical antibody or antigen-binding fragment thereof which lacks said mutation; wherein the mutation is determined to increase affinity for the Fc receptor or lectin (agonize binding) if the affinity of the antibody or antigen-binding fragment thereof comprising said mutation is higher than the affinity of the antibody or antigen-binding fragment thereof which lacks the mutation, and/or wherein the mutation is determined to decrease affinity for the Fc receptor or lectin (antagonize binding) if the affinity of antibody or antigen-binding fragment thereof comprising said mutation is lower than the affinity of the antibody or antigen-binding fragment thereof which lacks the mutation. For example, the affinity of the antibody or antigen-binding fragment thereof lacking the mutation can be determined in a similar manner in the antibody display system of the present invention or the affinity of it can be determined directly by measuring affinity by a known method such as ELISA, Biacore™ assay or a competition assay. In an embodiment of the invention, the heavy chain immunoglobulin comprising the mutation (e.g., the Fc region of the immunoglobulin heavy chain, e.g., in the CH2 and/or CH3 domain of the heavy chain) is from a library source wherein the clones in the library comprises one or more mutations in the heavy chain (e.g., in the Fc region of the immunoglobulin heavy chain, e.g., in the CH2 and/or CH3 domain of the heavy chain).

In an embodiment of the invention, cells expressing bait/antigen-binding fragment or bait/antibody tethered to the cell by an anchor such as SED1 that bind to an antigen can be detected by incubating the cells with fluorescently labeled antigen (e.g., biotin label) and sorting/selecting cells that specifically bind the antigen by fluorescence-activated cell sorting (FACS). Thus, in an embodiment of the invention, the eukaryotic host cells expressing the bait/antigen-binding fragment or bait/antibody bound with the antigen are identified and sorted using fluorescence-activated cell sorting (FACS). For example, in an embodiment of the invention, cells expressing the bait/antigen-binding fragment or bait/antibody bound to the antigen on the cell surface are labeled with a fluorescent antigen or fluorescent secondary antibody that also binds to the antigen. The fluorescent label is detected during the FACS sorting and used as the signal for sorting. Labeled cells indicate the presence of a cell surface expressed bait/antigen-binding fragment or bait/antibody bound to antigen and are collected in one vessel whereas cells not expressing signal are collected in a separate vessel. The present invention, accordingly, includes a method comprising the following steps for determining if an antibody or antigen-binding fragment thereof from a library specifically binds to an antigen:

(1) Transform:
   (i) one or more immunoglobulin libraries, containing polynucleotides encoding light and heavy chain immunoglobulins;
   (ii) one or more immunoglobulin libraries, containing polynucleotides encoding light chain immunoglobulins and a single clonal heavy chain immunoglobulin; or
   (iii) one or more immunoglobulin libraries, containing polynucleotides encoding heavy chain immunoglobulins and a single clonal light chain immunoglobulin;
   wherein, said chains are capable of forming an antibody or antigen-binding fragment thereof, into a eukaryotic host cell comprising polynucleotides encoding the bait (e.g., *Pichia pastoris*);
(2) Grow transformed cells in a liquid culture medium;
(3) Allow expression of the bait on the surface of the cells;
(4) Label the cells with fluorescently labeled antigen or antigen bound to a fluorescently labeled secondary antibody;
(5) Sort and isolate fluorescently labeled cells using FACS for one round;
(6) Regrow the labeled, sorted cells;
(7) Allow expression of the bait in the cells;
(8) Label the cells with fluorescently labeled antigen or antigen bound to a fluorescently labeled secondary antibody;
(9) Sort and isolate fluorescently labeled cells using FACS for a second round;
(10) Regrow the labeled, sorted cells on solid culture medium so that individual cellular clones grow into discrete cellular colonies;
(11) Identify colonies with affinity for the antigen;
(12) Grow cells from identified colonies in a liquid culture medium and isolate supernatant containing full, non-tethered antibody or antigen-binding fragment thereof comprising the immunoglobulin light and heavy chains; wherein, expression of the bait is optionally inhibited;
(13) Determine affinity of non-tethered antibodies or antigen-binding fragments thereof, from the supernatant, for the antigen and identify clones with acceptable affinity (e.g., by Biacore™ analysis);
(14) Determine the nucleotide sequence of polynucleotides in the identified clones encoding the heavy and light chain immunoglobulins.

The scope of the present invention also includes a method for identifying polynucleotides encoding a heavy chain and light chain immunoglobulin of an antibody or antigen-binding fragment thereof or for identifying an antibody or antigen-binding fragment thereof which exhibits high stability. Such a method comprises the following steps:

(a) co-expressing the bait and the polynucleotides encoding the heavy and light chains in a eukaryotic host cell (e.g., *Pichia pastoris*) while subjecting antibodies comprising said chains to a denaturant;

In an embodiment of the invention, a denaturant is present in a concentration or amount or magnitude (e.g., at a sufficiently high temperature) that a practitioner of ordinary skill in the art would expect to, at least partially, denature an antibody and, thus, inhibit its ability to bind to an antigen. For example, possible denaturants include urea (e.g., 2, 3, 4, 5 or 6 M or more), detergent such as triton X-100 (e.g., 1% or more), dithiothreitol (DTT) (e.g., 250 mM or 500 mM or more), guanidine hydrochloride, light (e.g., ultraviolet or visible), extreme pH (e.g., 1, 2, 3, 14, 13 or 12) or a temperature above about 4° C., such as 37° C. (e.g., 42° C., 48° C. or 50° C.) or any combination thereof (e.g., 500 mM DTT/6 M urea).

(b) identifying a eukaryotic host cell expressing bait/antigen-binding fragment or bait/antibody that has detectable affinity (e.g., acceptable affinity) for the antigen;

In an embodiment of the invention, full antibodies comprising light and heavy chain variable regions identical to those complexed with the bait are also analyzed to determine if they possess detectable affinity.

In an embodiment of the invention, the full antibodies are secreted from the host cell. In an embodiment of the invention, the full antibodies are isolated from the host cell.

In an embodiment of the invention, expression of the bait in the host cell is inhibited, but expression of the full antibodies is not inhibited. In this embodiment of the invention, the host cell expresses only the full antibody but does not express the bait at any significant quantity. Once expression of the bait is inhibited, in an embodiment of the invention, the full antibody produced from the host cell is analyzed to determine if it possesses detectable affinity (e.g., acceptable affinity); and, (c) identifying said antibodies or polynucleotides encoding the heavy and light chains from the cell wherein one or more of the polynucleotides are optionally isolated from the host cell; wherein antibodies exhibiting affinity for the antigen in the presence of denaturant are determined to exhibit high stability. In an embodiment of the invention, the nucleotide sequence of the polynucleotide is determined.

In an embodiment of the invention, sed1p is *Saccharomyces cerevisiae* sed1p which, in an embodiment of the invention, comprises the following amino acid sequence: (SEQ ID NO:1)

VDQFSNSTSASSTDVTSSSSISTSSGSVTITSSEAPESDNGTSTAAPTET
STEAPTTAIPTNGTSTEAPTTAIPTNGTSTEAPTDTTTEAPTTALPTNGT
STEAPTDTTTEAPTTGLPTNGTTSAFPPTTSLPPSNTTTTPPYNPSTDYT
TDYTVVTEYTTYCPEPTTFTTNGKTYTVTEPTTLTITDCPCTIEKPTTTS
TTEYTVVTEYTTYCPEPTTFTTNGKTYTVTEPTTLTITDCPCTIEKSEAP
ESSVPVTESKGTTTKETGVTTKQTTANPSLTVSTVVPVSSSASSHSVVIN
SNGANVVVPGALGLAGVAMLFL.

The corresponding nucleotide sequence (SED-1) encoding sed1p is (SEQ ID NO:2):

CAATTCTCTAACTCTACTTCCGCTTCCTCTACTGACGTTACTTCCTCCTC
CTCTATTTCTACTTCCTCCGGTTCCGTTACTATTACTTCCTCTGAGGCTC
CAGAATCTGACAACGGTACTTCTACTGCTGCTCCAACTGAAACTTCTACT
GAGGCTCCTACTACTGCTATTCCAACTAACGGAACTTCCACAGAGGCTCC
AACAACAGCTATCCCTACAAACGGTACATCCACTGAAGCTCCTACTGACA
CTACTACAGAAGCTCCAACTACTGCTTTGCCTACTAATGGTACATCAACA
GAGGCTCCTACAGATACAACAACTGAAGCTCCAACAACTGGATTGCCAAC
AAACGGTACTACTTCTGCTTTCCCACCAACTACTTCCTTGCCACCATCCA
ACACTACTACTACTCCACCATACAACCCATCCACTGACTACACTACTGAC
TACACAGTTGTTACTGAGTACACTACTTACTGTCCAGAGCCAACTACTTT
CACAACAAACGGAAAGACTTACACTGTTACTGAGCCTACTACTTTGACTA
TCACTGACTGTCCATGTACTATCGAGAAGCCAACTACTACTTCCACTACA
GAGTATACTGTTGTTACAGAATACACAACATATTGTCCTGAGCCAACAAC
ATTCACTACTAATGGAAAAACATACACAGTTACAGAACCAACTACATTGA
CAATTACAGATTGTCCTTGTACAATTGAGAAGTCCGAGGCTCCTGAATCT
TCTGTTCCAGTTACTGAATCCAAGGGTACTACTACTAAAGAAACTGGTGT
TACTACTAAGCAGACTACTGCTAACCCATCCTTGACTGTTTCCACTGTTG
TTCCAGTTTCTTCCTCTGCTTCTTCCCACTCCGTTGTTATCAACTCCAAC
GGTGCTAACGTTGTTGTTCCTGGTGCTTTGGGATTGGCTGGTGTTGCTAT
GTTGTTCTTG

In an embodiment of the invention, the bait is linked to a signal sequence such as an alpha mating factor signal sequence of *Saccharomyces cerevisiae* (e.g., MRFPSIFTAV-LFAASSALA (SEQ ID NO: 3)), encoded by nucleotide sequence SEQ ID NO:4:

ATGAGATTCCCATCCATCTTCACTGCTGTTTTGTTCGCTGCTTCCTCTGC
TTTGGCT.

In an embodiment of the invention, the bait comprising the human light chain immunoglobulin domain fused to a Sed1p polypeptide comprises the amino acid sequence (SEQ ID NO: 5) with the light chain immunoglobulin domain underlined and the linker is in bold, followed by the Sed1p sequence:

<u>DIQMTQSPSSLSASVGDRVTITCKASQNVGTNVVWYQQKPGKAPKALIHS</u>
<u>ASYRYSGVPSRFSGSGSGTDFTLTISSLQPEDFATYYCQQYKTYPYTFGQ</u>
<u>GTKVEIKRTVAAPSVFIFPPSDEQLKSGTASVVCLLNNFYPREAKVQWKV</u>
<u>DNALQSGNSQESVTEQDSKDSTYSLSSTLTLSKADYEKHKVYACEVTHQG</u>
<u>LSSPVTKSFNRGEC</u>GGGGSGGGGSGGGGSVDQFSNSTSASSTDVTSSSSI
STSSGSVTITSSEAPESDNGTSTAAPTETSTEAPTTAIPTNGTSTEAPTT
AIPTNGTSTEAPTDTTTEAPTTALPTNGTSTEAPTDTTTEAPTTGLPTNG
TTSAFPPTTSLPPSNTTTTPPYNPSTDYTTDYTVVTEYTTYCPEPTTFTT
NGKTYTVTEPTTLTITDCPCTIEKPTTTSTTEYTVVTEYTTYCPEPTTFT
TNGKTYTVTEPTTLTITDCPCTIEKSEAPESSVPVTESKGTTTKETGVTT
KQTTANPSLTVSTVVPVSSSASSHSVVINSNGANVVVPGALGLAGVAMLF
L

The corresponding nucleotide sequence encoding SEQ ID NO: 5 is SEQ ID NO:6 (with light chain sequence underlined, the linker sequence in bold, followed by the SED-1 sequence in plain text):

<u>GACATTCAAATGACTCAGTCCCCATCTTCCTTGTCTGCTTCCGTTGGTGA</u>
<u>CAGAGTTACTATCACTTGTAAGGCTTCCCAGAACGTTGGAACTAACGTTG</u>
<u>TTTGGTATCAGCAGAAGCCAGGTAAGGCTCCAAAGGCTTTGATTCACTCC</u>
<u>GCTTCATACAGATACTCCGGTGTTCCATCCAGATTCTCTGGTTCTGGTTC</u>
<u>CGGTACTGACTTTACTTTGACTATCTCCTCATTGCAGCCAGAGGACTTCG</u>
<u>CTACTTACTACTGTCAGCAGTACAAGACTTACCCATACACTTTCGGTCAG</u>
<u>GGTACCAAGGTTGAGATCAAGAGAACTGTTGCTGCTCCATCCGTTTTCAT</u>
<u>TTTCCCACCATCCGACGAACAGTTGAAGTCTGGTACAGCTTCCGTTGTTT</u>
<u>GTTTGTTGAACAACTTCTACCCAAGAGAGGCTAAGGTTCAGTGGAAGGTT</u>
<u>GACAACGCTTTGCAATCCGGTAACTCCCAAGAATCCGTTACTGAGCAAGA</u>
<u>CTCTAAGGACTCCACTTACTCCTTGTCCTCCACTTTGACTTTGTCCAAGG</u>
<u>CTGATTACGAGAAGCACAAGGTTTACGCTTGTGAGGTTACACATCAGGGT</u>
<u>TTGTCCTCCCCAGTTACTAAGTCCTTCAACAGAGGAGAGTGT</u>GGTGGTGG
TGGTTCCGGTGGTGGTGGTTCTGGTGGTGGTGGTTCTCAATTCTCTAACT
CTACTTCCGCTTCCTCTACTGACGTTACTTCCTCCTCTATTTCTACT
TCCTCCGGTTCCGTTACTATTACTTCCTCTGAGGCTCCAGAATCTGACAA
CGGTACTTCTACTGCTGCTCCAACTGAAACTTCTACTGAGGCTCCTACTA
CTGCTATTCCAACTAACGGAACTTCCACAGAGGCTCCAACAACAGCTATC
CCTACAAACGGTACATCCACTGAAGCTCCTACTGACACTACTACAGAAGC
TCCAACTACTGCTTTGCCTACTAATGGTACATCAACAGAGGCTCCTACAG
ATACAACAACTGAAGCTCCAACAACTGGATTGCCAACAAACGGTACTACT
TCTGCTTTCCCACCAACTACTTCCTTGCCACCATCCAACACTACTACTAC

-continued
TCCACCATACAACCCATCCACTGACTACACTACTGACTACACAGTTGTTA

CTGAGTACACTACTTACTGTCCAGAGCCAACTACTTTCACAACAAACGGA

AAGACTTACACTGTTACTGAGCCTACTACTTTGACTATCACTGACTGTCC

ATGTACTATCGAGAAGCCAACTACTACTTCCACTACAGAGTATACTGTTG

TTACAGAATACACAACATATTGTCCTGAGCCAACAACATTCACTACTAAT

GGAAAAACATACACAGTTACAGAACCAACTACATTGACAATTACAGATTG

TCCTTGTACAATTGAGAAGTCCGAGGCTCCTGAATCTTCTGTTCCAGTTA

CTGAATCCAAGGGTACTACTACTAAAGAAACTGGTGTTACTACTAAGCAG

ACTACTGCTAACCCATCCTTGACTGTTTCCACTGTTGTTCCAGTTTCTTC

CTCTGCTTCTTCCCACTCCGTTGTTATCAACTCCAACGGTGCTAACGTTG

TTGTTCCTGGTGCTTTGGGATTGGCTGGTGTTGCTATGTTGTTCTTG

EXAMPLES

The present invention is intended to exemplify the present invention and not to be a limitation thereof. The methods and compositions (e.g., polypeptides, polynucleotides, plasmids, yeast cells) disclosed below fall within the scope of the present invention.

Example 1

Construction of Expression Cassettes

A polynucleotide encoding the N-terminus of a cell surface anchoring protein *S. cerevisiae* Sed1p that inherently contains an attached glycophosphotidylinositol (GPI) post-translational modification that anchors the protein on the yeast cell wall was linked to a nucleic acid sequence that encodes the human IgG2 anti PCSK9 (1F11) Light Chain (Lc).

The plasmid pGLY11714 containing anti-PCSK9 Lc bait cassette was constructed using a codon optimized sequence of human IgG2 Lc (VL+CL) fragment, which was synthesized and fused in frame to the 3' end of the nucleic acid sequence of *S. cerevisiae* α-mating factor signal sequence. The nucleic acid sequence of three of the (GGGS, SEQ ID NO:10) linker was used to link the nucleic acid sequence of Lc 3' end to the 5' end of *S. cerevisiae* Sed1p. The construct was subcloned into pGLY9008 at EcoRI-SalI (replacing the Fc) by the contracting research organization (CRO) Genewiz. As in the above example, the resulting plasmid enables delivery of the Lc-SED1 cassette under the control of the *Pichia pastoris* AOX1 promoter at the URA6 locus in *Pichia pastoris*.

Nucleic Acid Sequence of pGLY11714 (SEQ ID NO: 7)

TCGCGCGTTTCGGTGATGACGGTGAAAACCTCTGACACATGCAGCTCCCG

GAGACGGTCACAGCTTGTCTGTAAGCGGATGCCGGGAGCAGACAAGCCCG

TCAGGGCGCGTCAGCGGGTGTTGGCGGGTGTCGGGGCTGGCTTAACTATG

CGGCATCAGAGCAGATTGTACTGAGAGTGCACCATATGCGGTGTGAAATA

CCGCACAGATGCGTAAGGAGAAAATACCGCATCAGGCGCCATTCGCCATT

CAGGCTGCGCAACTGTTGGGAAGGGCGATCGGTGCGGGCCTCTTCGCTAT

TACGCCAGCTGGCGAAAGGGGGATGTGCTGCAAGGCGATTAAGTTGGGTA

ACGCCAGGGTTTTCCCAGTCACGACGTTGTAAAACGACGGCCAGTGAATT

GAGATCTAACATCCAAAGACGAAAGGTTGAATGAAACCTTTTTGCCATCC

GACATCCACAGGTCCATTCTCACACATAAGTGCCAAACGCAACAGGAGGG

GATACACTAGCAGCAGACCGTTGCAAACGCAGGACCTCCACTCCTCTTCT

CCTCAACACCCACTTTTGCCATCGAAAAACCAGCCCAGTTATTGGGCTTG

ATTGGAGCTCGCTCATTCCAATTCCTTCTATTAGGCTACTAACACCATGA

CTTTATTAGCCTGTCTATCCTGGCCCCCCTGGCGAGGTTCATGTTTGTTT

ATTTCCGAATGCAACAAGCTCCGCATTACACCCGAACATCACTCCAGATG

AGGGCTTTCTGAGTGTGGGGTCAAATAGTTTCATGTTCCCCAAATGGCCC

AAAACTGACAGTTTAAACGCTGTCTTGGAACCTAATATGACAAAAGCGTG

ATCTCATCCAAGATGAACTAAGTTTGGTTCGTTGAAATGCTAACGGCCAG

TTGGTCAAAAAGAAACTTCCAAAAGTCGGCATACCGTTTGTCTTGTTTGG

TATTGATTGACGAATGCTCAAAAATAATCTCATTAATGCTTAGCGCAGTC

TCTCTATCGCTTCTGAACCCCGGTGCACCTGTGCCGAAACGCAAATGGGG

AAACACCCGCTTTTTGGATGATTATGCATTGTCTCCACATTGTATGCTTC

CAAGATTCTGGTGGGAATACTGCTGATAGCCTAACGTTCATGATCAAAAT

TTAACTGTTCTAACCCCTACTTGACAGCAATATATAAACAGAAGGAAGCT

GCCCTGTCTTAAACCTTTTTTTTTATCATCATTATTAGCTTACTTTCATA

ATTGCGACTGGTTCCAATTGACAAGCTTTTGATTTTAACGACTTTTAACG

ACAACTTGAGAAGATCAAAAAACAACTAATTATTCGAAACGGAATTCACG

ATGAGATTCCCATCCATCTTCACTGCTGTTTTGTTCGCTGCTTCCTCTGC

TTTGGCTGACATTCAAATGACTCAGTCCCCATCTTCCTTGTCTGCTTCCG

TTGGTGACAGAGTTACTATCACTTGTAAGGCTTCCCAGAACGTTGGAACT

AACGTTGTTTGGTATCAGCAGAAGCCAGGTAAGGCTCCAAAGGCTTTGAT

TCACTCCGCTTCATACAGATACTCCGGTGTTCCATCCAGATTCTCTGGTT

CTGGTTCCGGTACTGACTTTACTTTGACTATCTCCTCATTGCAGCCAGAG

GACTTCGCTACTTACTACTGTCAGCAGTACAAGACTTACCCATACACTTT

CGGTCAGGGTACCAAGGTTGAGATCAAGAGAACTGTTGCTGCTCCATCCG

TTTTCATTTTCCCACCATCCGACGAACAGTTGAAGTCTGGTACAGCTTCC

GTTGTTTGTTTGTTGAACAACTTCTACCCAAGAGAGGCTAAGGTTCAGTG

GAAGGTTGACAACGCTTTGCAATCCGGTAACTCCCAAGAATCCGTTACTG

AGCAAGACTCTAAGGACTCCACTTACTCCTTGTCCTCCACTTTGACTTTG

TCCAAGGCTGATTACGAGAAGCACAAGGTTTACGCTTGTGAGGTTACACA

TCAGGGTTTGTCCTCCCCAGTTACTAAGTCCTTCAACAGAGGAGAGTGTG

GTGGTGGTGGTTCCGGTGGTGGTGGTTCTGGTGGTGGTGGTTCTGTCGAC

CAATTCTCTAACTCTACTTCCGCTTCCTCTACTGACGTTACTTCCTCCTC

CTCTATTTCTACTTCCTCCGGTTCCGTTACTATTACTTCCTCTGAGGCTC

CAGAATCTGACAACGGTACTTCTACTGCTGCTCCAACTGAAACTTCTACT

GAGGCTCCTACTACTGCTATTCCAACTAACGGAACTTCCACAGAGGCTCC

AACAACAGCTATCCCTACAAACGGTACATCCACTGAAGCTCCTACTGACA

-continued

CTACTACAGAAGCTCCAACTACTGCTTTGCCTACTAATGGTACATCAACA
GAGGCTCCTACAGATACAACAACTGAAGCTCCAACAACTGGATTGCCAAC
AAACGGTACTACTTCTGCTTTCCCACCAACTACTTCCTTGCCACCATCCA
ACACTACTACTACTCCACCATACAACCCATCCACTGACTACACTACTGAC
TACACAGTTGTTACTGAGTACACTACTTACTGTCCAGAGCCAACTACTTT
CACAACAAACGGAAAGACTTACACTGTTACTGAGCCTACTACTTTGACTA
TCACTGACTGTCCATGTACTATCGAGAAGCCAACTACTACTTCCACTACA
GAGTATACTGTTGTTACAGAATACACAACATATTGTCCTGAGCCAACAAC
ATTCACTACTAATGGAAAAACATACACAGTTACAGAACCAACTACATTGA
CAATTACAGATTGTCCTTGTACAATTGAGAAGTCCGAGGCTCCTGAATCT
TCTGTTCCAGTTACTGAATCCAAGGGTACTACTACTAAAGAAACTGGTGT
TACTACTAAGCAGACTACTGCTAACCCATCCTTGACTGTTTCCACTGTTG
TTCCAGTTTCTTCCTCTGCTTCTTCCCACTCCGTTGTTATCAACTCCAAC
GGTGCTAACGTTGTTGTTCCTGGTGCTTTGGGATTGGCTGGTGTTGCTAT
GTTGTTCTTGTAATAGGGCCGGCCATTTAAATACAGGCCCCTTTTCCTTT
GTCGATATCATGTAATTAGTTATGTCACGCTTACATTCACGCCCTCCTCC
CACATCCGCTCTAACCGAAAAGGAAGGAGTTAGACAACCTGAAGTCTAGG
TCCCTATTTATTTTTTTAATAGTTATGTTAGTATTAAGAACGTTATTTA
TATTTCAAATTTTTCTTTTTTTCTGTACAAACGCGTGTACGCATGTAAC
ATTATACTGAAAACCTTGCTTGAGAAGGTTTTGGGACGCTCGAAGGCTTT
AATTTGCAAGCTGGATCCGCGGCCGCTTACGCGCCGTTCTTCGCTTGGTC
TTGTATCTCCTTACACTGTATCTTCCCATTTGCGTTTAGGTGGTTATCAA
AAACTAAAAGGAAAAATTTCAGATGTTTATCTCTAAGGTTTTTTCTTTTT
ACAGTATAACACGTGATGCGTCACGTGGTACTAGATTACGTAAGTTATTT
TGGTCCGGTGGGTAAGTGGGTAAGAATAGAAAGCATGAAGGTTTACAAAA
ACGCAGTCACGAATTATTGCTACTTCGAGCTTGGAACCACCCCAAAGATT
ATATTGTACTGATGCACTACCTTCTCGATTTTGCTCCTCCAAGAACCTAC
GAAAAACATTTCTTGAGCCTTTTCAACCTAGACTACACATCAAGTTATTT
AAGGTATGTTCCGTTAACATGTAAGAAAAGGAGAGGATAGATCGTTTATG
GGGTACGTCGCCTGATTCAAGCGTGACCATTCGAAGAATAGGCCTTCGAA
AGCTGAATAAAGCAAATGTCAGTTGCGATTGGTATGCTGACAAATTAGCA
TAAAAAGCAATAGACTTTCTAACCACCTGTTTTTTTCCTTTTACTTTATT
TATATTTTGCCACCGTACTAACAAGTTCAGACAAATTAATTAACACCATG
TCAGAAGATCAAAAAGTGAAAATTCCGTACCTTCTAAGGTTAATATGGT
GAATCGCACCGATATACTGACTACGATCAAGTCATTGTCATGGCTTGACT
TGATGTTGCCATTTACTATAATTCTCTCCATAATCATTGCAGTAATAATT
TCTGTCTATGTGCCTTCTTCCCGTCACACTTTTGACGCTGAAGGTCATCC
CAATCTAATGGGAGTGTCCATTCCTTTGACTGTTGGTATGATTGTAATGA
TGATTCCCCGATCTGCAAAGTTTCCTGGGAGTCTATTCACAAGTACTTC
TACAGGAGCTATATAAGGAAGCAACTAGCCCTCTCGTTATTTTTGAATTG
GGTCATCGGTCCTTTGTTGATGACAGCATTGGCGTGGATGGCGCTATTCG

-continued

ATTATAAGGAATACCGTCAAGGCATTATTATGATCGGAGTAGCTAGATGC
ATTGCCATGGTGCTAATTTGGAATCAGATTGCTGGAGGAGACAATGATCT
CTGCGTCGTGCTTGTTATTACAAACTCGCTTTTACAGATGGTATTATATG
CACCATTGCAGATATTTTACTGTTATGTTATTTCTCATGACCACCTGAAT
ACTTCAAATAGGGTATTATTCGAAGAGGTTGCAAAGTCTGTCGGAGTTTT
TCTCGGCATACCACTGGGAATTGGCATTATCATACGTTTGGGAAGTCTTA
CCATAGCTGGTAAAAGTAATTATGAAAAATACATTTTGAGATTTATTTCT
CCATGGGCAATGATCGGATTTCATTACACTTTATTTGTTATTTTTATTAG
TAGAGGTTATCAATTTATCCACGAAATTGGTTCTGCAATATTGTGCTTTG
TCCCATTGGTGCTTTACTTCTTTATTGCATGGTTTTTGACCTTCGCATTA
ATGAGGTACTTATCAATATCTAGGAGTGATACACAAAGAGAATGTAGCTG
TGACCAAGAACTACTTTTAAAGAGGGTCTGGGGAAGAAAGTCTTGTGAAG
CTAGCTTTTCTATTACGATGACGCAATGTTTCACTATGGCTTCAAATAAT
TTTGAACTATCCCTGGCAATTGCTATTTCCTTATATGGTAACAATAGCAA
GCAAGCAATAGCTGCAACATTTGGGCCGTTGCTAGAAGTTCCAATTTTAT
TGATTTTGGCAATAGTCGCGAGAATCCTTAAACCATATTATATATGGAAC
AATAGAAATTAATTAACAGGCCCCTTTTCCTTTGTCGATATCATGTAATT
AGTTATGTCACGCTTACATTCACGCCCTCCTCCCACATCCGCTCTAACCG
AAAAGGAAGGAGTTAGACAACCTGAAGTCTAGGTCCCTATTTATTTTTTT
TAATAGTTATGTTAGTATTAAGAACGTTATTTATATTTCAAATTTTTCTT
TTTTTTCTGTACAAACGCGTGTACGCATGTAACATTATACTGAAAACCTT
GCTTGAGAAGGTTTTGGGACGCTCGAAGGCTTTAATTTGCAAGCTGCGGC
CTAAGGCGCGCCAGGCCATAATGGCCCAAATGCAAGAGGACATTAGAAAT
GTGTTTGGTAAGAACATGAAGCCGGAGGCATACAAACGATTCACAGATTT
GAAGGAGGAAAACAAACTGCATCCACCGGAAGTGCCAGCAGCCGTGTATG
CCAACCTTGCTCTCAAAGGCATTCCTACGGATCTGAGTGGGAAATATCTG
AGATTCACAGACCCACTATTGGAACAGTACCAAACCTAGTTTGGCCGATC
CATGATTATGTAATGCATATAGTTTTTGTCGATGCTCACCCGTTTCGAGT
CTGTCTCGTATCGTCTTACGTATAAGTTCAAGCATGTTTACCAGGTCTGT
TAGAAACTCCTTTGTGAGGGCAGGACCTATTCGTCTCGGTCCCGTTGTTT
CTAAGAGACTGTACAGCCAAGCGCAGAATGGTGGCATTAACCATAAGAGG
ATTCTGATCGGACTTGGTCTATTGGCTATTGGAACCACCCTTTACGGGAC
AACCAACCCTACCAAGACTCCTATTGCATTTGTGGAACCAGCCACGGAAA
GAGCGTTTAAGGACGGAGACGTCTCTGTGATTTTTGTTCTCGGAGGTCCA
GGAGCTGGAAAAGGTACCCAATGTGCCAAACTAGTGAGTAATTACGGATT
TGTTCACCTGTCAGCTGGAGACTTGTTACGTGCAGAACAGAAGAGGGAGG
GGTCTAAGTATGGAGAGATGATTTCCCAGTATATCAGAGATGGACTGATA
GTACCTCAAGAGGTCACCATTGCGCTCTTGGAGCAGGCCATGAAGGAAAA
CTTCGAGAAAGGGAAGACACGGTTCTTGATTGATGGATTCCCTCGTAAGA
TGGACCAGGCCAAAACTTTTGAGGAAAAAGTCGCAAAGTCCAAGGTGACA

-continued

```
CTTTTCTTTGATTGTCCCGAATCAGTGCTCCTTGAGAGATTACTTAAAAG
AGGACAGACAAGCGGAAGAGAGGATGATAATGCGGAGAGTATCAAAAAAA
GATTCAAAACATTCGTGGAAACTTCGATGCCTGTGGTGGACTATTTCGGG
AAGCAAGGACGCGTTTTGAAGGTATCTTGTGACCACCCTGTGGATCAAGT
GTATTCACAGGTTGTGTCGGTGCTAAAAGAGAAGGGGATCTTTGCCGATA
ACGAGACGGAGAATAAATAAACATTGTAATAAGATTTAGACTGTGAATGT
TCTATGTAATATTTTTCGAGATACTGTATCTATCTGGTGTACCGTATCAC
TCTGGACTTGCAAACTCATTGATTACTTGTGCAATGGGCAAGAAGGATAG
CTCTAGAAAGAAGAAGAAAAAGGAGCCGCCTGAAGAGCTGGATCTTTCCG
AGGTTGTTCCAACTTTTGGTTATGAGGAATTTCATGTTGAGCAAGAGGAG
AATCCGGTCGATCAAGACGAACTTGACGGCCATAATGGCCTAGCTTGGCG
TAATCATGGTCATAGCTGTTTCCTGTGTGAAATTGTTATCCGCTCACAAT
TCCACACAACATACGAGCCGGAAGCATAAAGTGTAAAGCCTGGGGTGCCT
AATGAGTGAGCTAACTCACATTAATTGCGTTGCGCTCACTGCCCGCTTTC
CAGTCGGGAAACCTGTCGTGCCAGCTGCATTAATGAATCGGCCAACGCGC
GGGGAGAGGCGGTTTGCGTATTGGGCGCTCTTCCGCTTCCTCGCTCACTG
ACTCGCTGCGCTCGGTCGTTCGGCTGCGGCGAGCGGTATCAGCTCACTCA
AAGGCGGTAATACGGTTATCCACAGAATCAGGGGATAACGCAGGAAAGAA
CATGTGAGCAAAAGGCCAGCAAAAGGCCAGGAACCGTAAAAAGGCCGCGT
TGCTGGCGTTTTTCCATAGGCTCCGCCCCCCTGACGAGCATCACAAAAAT
CGACGCTCAAGTCAGAGGTGGCGAAACCCGACAGGACTATAAAGATACCA
GGCGTTTCCCCCTGGAAGCTCCCTCGTGCGCTCTCCTGTTCCGACCCTGC
CGCTTACCGGATACCTGTCCGCCTTTCTCCCTTCGGGAAGCGTGGCGCTT
TCTCATAGCTCACGCTGTAGGTATCTCAGTTCGGTGTAGGTCGTTCGCTC
CAAGCTGGGCTGTGTGCACGAACCCCCCGTTCAGCCCGACCGCTGCGCCT
TATCCGGTAACTATCGTCTTGAGTCCAACCCGGTAAGACACGACTTATCG
CCACTGGCAGCAGCCACTGGTAACAGGATTAGCAGAGCGAGGTATGTAGG
CGGTGCTACAGAGTTCTTGAAGTGGTGGCCTAACTACGGCTACACTAGAA
GGACAGTATTTGGTATCTGCGCTCTGCTGAAGCCAGTTACCTTCGGAAAA
AGAGTTGGTAGCTCTTGATCCGGCAAACAAACCACCGCTGGTAGCGGTGG
TTTTTTTGTTTGCAAGCAGCAGATTACGCGCAGAAAAAAAGGATCTCAAG
AAGATCCTTTGATCTTTTCTACGGGGTCTGACGCTCAGTGGAACGAAAAC
TCACGTTAAGGGATTTTGGTCATGAGATTATCAAAAAGGATCTTCACCTA
GATCCTTTTAAATTAAAAATGAAGTTTTAAATCAATCTAAAGTATATATG
AGTAAACTTGGTCTGACAGTTACCAATGCTTAATCAGTGAGGCACCTATC
TCAGCGATCTGTCTATTTCGTTCATCCATAGTTGCCTGACTCCCCGTCGT
GTAGATAACTACGATACGGGAGGGCTTACCATCTGGCCCCAGTGCTGCAA
TGATACCGCGAGACCCACGCTCACCGGCTCCAGATTTATCAGCAATAAAC
CAGCCAGCCGGAAGGGCCGAGCGCAGAAGTGGTCCTGCAACTTTATCCGC
CTCCATCCAGTCTATTAATTGTTGCCGGGAAGCTAGAGTAAGTAGTTCGC
CAGTTAATAGTTTGCGCAACGTTGTTGCCATTGCTACAGGCATCGTGGTG
TCACGCTCGTCGTTTGGTATGGCTTCATTCAGCTCCGGTTCCCAACGATC
AAGGCGAGTTACATGATCCCCATGTTGTGCAAAAAAGCGGTTAGCTCCT
TCGGTCCTCCGATCGTTGTCAGAAGTAAGTTGGCCGCAGTGTTATCACTC
ATGGTTATGGCAGCACTGCATAATTCTCTTACTGTCATGCCATCCGTAAG
ATGCTTTTCTGTGACTGGTGAGTACTCAACCAAGTCATTCTGAGAATAGT
GTATGCGGCGACCGAGTTGCTCTTGCCCGGCGTCAATACGGGATAATACC
GCGCCACATAGCAGAACTTTAAAAGTGCTCATCATTGGAAAACGTTCTTC
GGGGCGAAAACTCTCAAGGATCTTACCGCTGTTGAGATCCAGTTCGATGT
AACCCACTCGTGCACCCAACTGATCTTCAGCATCTTTTACTTTCACCAGC
GTTTCTGGGTGAGCAAAAACAGGAAGGCAAAATGCCGCAAAAAAGGGAAT
AAGGGCGACACGGAAATGTTGAATACTCATACTCTTCCTTTTTCAATATT
ATTGAAGCATTTATCAGGGTTATTGTCTCATGAGCGGATACATATTTGAA
TGTATTTAGAAAAATAAACAAATAGGGGTTCCGCGCACATTTCCCCGAAA
AGTGCCACCTGACGTCTAAGAAACCATTATTATCATGACATTAACCTATA
AAAATAGGCGTATCACGAGGCCCTTTCGTC
```

Amino Acid Sequence of Anti-PCSK9 Light Chain (SEQ ID NO:8)

DIQMTQSPSSLSASVGDRVTITCKASQNVGTNVVWYQQKPGKAPKALIHS
ASYRYSGVPSRFSGSGSGTDFTLTISSLQPEDFATYYCQQYKTYPYTFGQ
GTKVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC

Amino Acid Sequence of Alpha Mating Factor-antipPCSK9 Lc-(GGGS, SEQ ID NO:10) Linker-S. cerevisiae Sed1p (SEQ ID NO:9)

MRFPSIFTAVLFAASSALA<u>DIQMTQSPSSLSASVGDRVTITCKASQNVGT</u>
<u>NVVWYQQKPGKAPKALIHSASYRYSGVPSRFSGSGSGTDFTLTISSLQPE</u>
<u>DFATYYCQQYKTYPYTFGQGTKVEIKRTVAAPSVFIFPPSDEQLKSGTAS</u>
<u>VVCLLNNFYPREAKVQWKVDNALQSGNSQESVTEQDSKDSTYSLSSTLTL</u>
<u>SKADYEKHKVYACEVTHQGLSSPVTKSFNRGEC</u>GGGGSGGGGSGGGGSVD
QFSNSTSASSTDVTSSSSISTSSGSVTITSSEAPESDNGTSTAAPTETST
EAPTTAIPTNGTSTEAPTTAIPTNGTSTEAPTDTTTEAPTTALPTNGTST
EAPTDTTTEAPTTGLPTNGTTSAFPPTTSLPPSNTTTTPPYNPSTDYTTD
YTVVTEYTTYCPEPTTFTTNGKTYTVTEPTTLTITDCPCTIEKPTTTSTT
EYTVVTEYTTYCPEPTTFTTNGKTYTVTEPTTLTITDCPCTIEKSEAPES
SVPVTESKGTTTKETGVTTKQTTANPSLTVSTVVPVSSSASSHSVVINSN
GANVVVPGALGLAGVAMLFL

Example 2

Glycoengineered Monoclonal Antibody Production Strains

To test this system for displaying full length antibodies (comprising human IgGs) on the yeast cell wall, pGLY11714 was introduced into *Pichia pastoris* strains that were previously selected and created as expression hosts of human anti-Her2 or anti-PCSK9 IgGs (as described in PCT/US2011/62286). An empty *Pichia pastoris* strain was included as a control. Different IgG forms (IgG1, IgG2 and IgG4) were included in this study to establish the ability to capture the different antibody forms.

TABLE 1

Strains Used

| Strain | Anti-body | IgG form |
|---|---|---|
| YGLY8316 | Null | Null |
| YGLY13979 | Anti-Her2 | Human IgG1 |
| YGLY21352 | Anti-PCSK9 | Human IgG2 |
| YGLY23236 | Anti-PCSK9 | Human IgG4 |
| YGLY22982 | Anti-PCSK9 | Human IgG2(F243A/V264A) Sialylated |
| YGLY25266 | Anti-PCSK9 | Human IgG2(F243A/V264A/S267E/L328F) Sialylated |

The glycoengineered *Pichia pastoris* monoclonal antibody production strains in Table 1 were grown in 50 mL BMGY media until the culture optical density, at 600 nm, was 2. The cells were washed three times with 1 M sorbitol and resuspended in 1 mL 1 M sorbitol. About 1-2 micrograms of SpeI linearized pGLY11714 was mixed with these competent cells. Transformation was performed with a Bio-Rad electroporation apparatus using the manufacturer's program specific for electroporation of nucleic acids into *Pichia pastoris*. One milliliter of recovery media was added to the cells, which were then plated out on yeast-soytone-dextrose (YSD) media with 50 μg/mL arsenite.

Example 3

Growth and Induction of Lc-Sed1p Displaying Yeast

By detecting the Fc fragment on the cell surface, it could be established that antibodies could be displayed using the Lc-Sed1p system, since the only way for the Fc to be displayed on cell surface is through heterodimerization of both the light chain to the heavy chain. To this end glycoengineered yeast expressing human IgGs and the Lc-SED1 bait expression cassette were inoculated using 600 μL BMGY in a 96 deep well plate or 50 mL BMGY in a 250 mL shake flasks for two days. The cells were collected by centrifugation and the supernatant was discarded. The cells were induced by incubation in 300 μL or 25 mL BMMY with PMTi inhibitor overnight following the methods described in International Patent Application Publication No. WO2007/061631.

Example 4

Flow Cytometry Detection of Surface Displayed Antibodies

To determine the efficiency of surface displaying antibodies using this method, cells were labeled with APC 635 labeled mouse anti-Human Fc, which detects the Fc fragment of human antibody molecules, and were processed by flow cytometry. Briefly, each culture, after growth to an optical density of 2 at 600 nm was pelleted by centrifugation and washed in 100 μL PBS. Cells were incubated for 30 minutes at room temperature (RT) in 100 μL phosphate buffer saline (PBS) containing fluorescently labeled (APC635) mouse anti-human Fc and washed in 100 μl PBS. One hundred microliters of PBS was used to resuspend pellets before analyzing in a flow cytometer. (See FIGS. 3A-D).

Figure 3A:
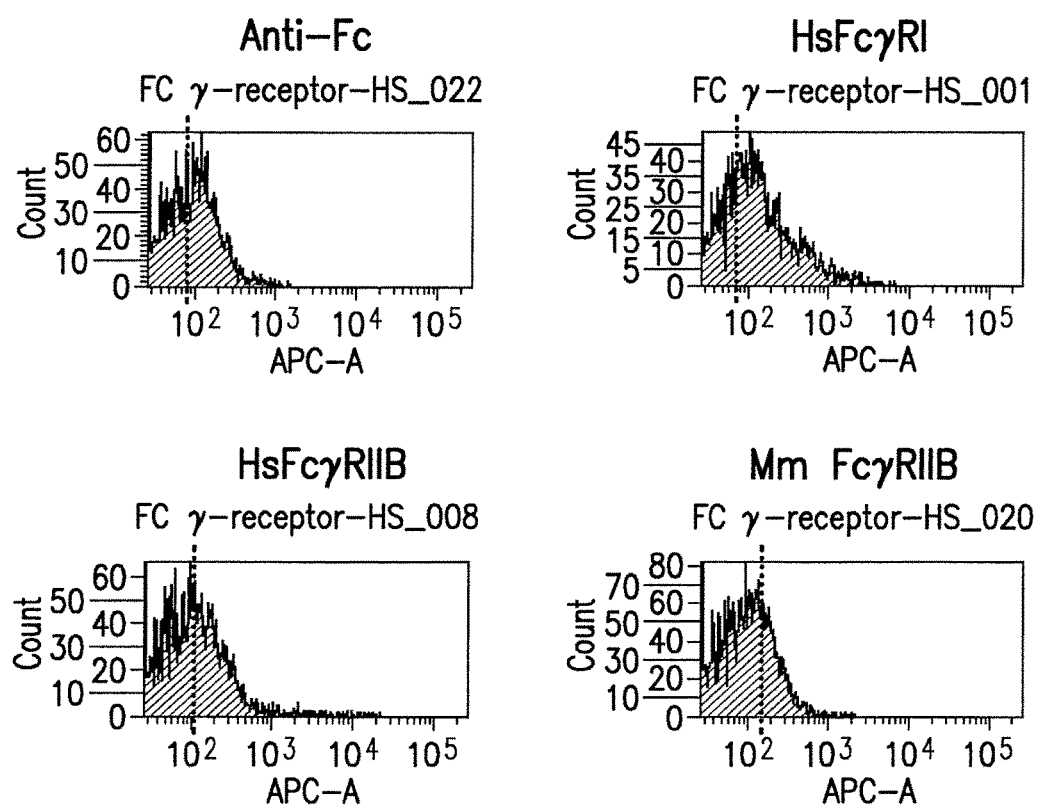
FIGS. 3A-D: FACS analysis of glycoengineered yeast expressing human IgGs and the Lc-SED1 bait expression cassette. The engineered cell cultures were induced by incubation BMMY with PMTi inhibitor. Cells were labeled with APC 635 labeled mouse anti-Human Fc, and His tagged: Hs FcγRI, Hs FcγRIIB, or Mm FcγRIIB followed by DyeLight 488 labeled anti-His and assayed by flow cytometry to detect Fc binding of displayed IgGs.
Figure 3B:
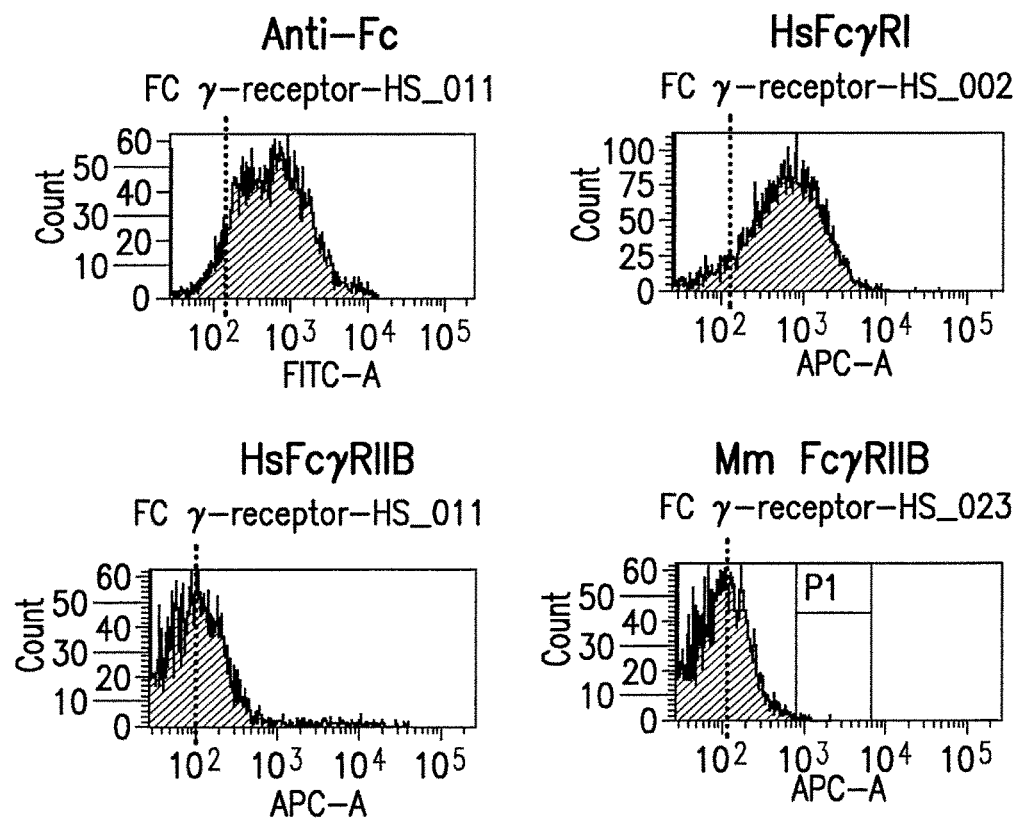
Figure 3C:
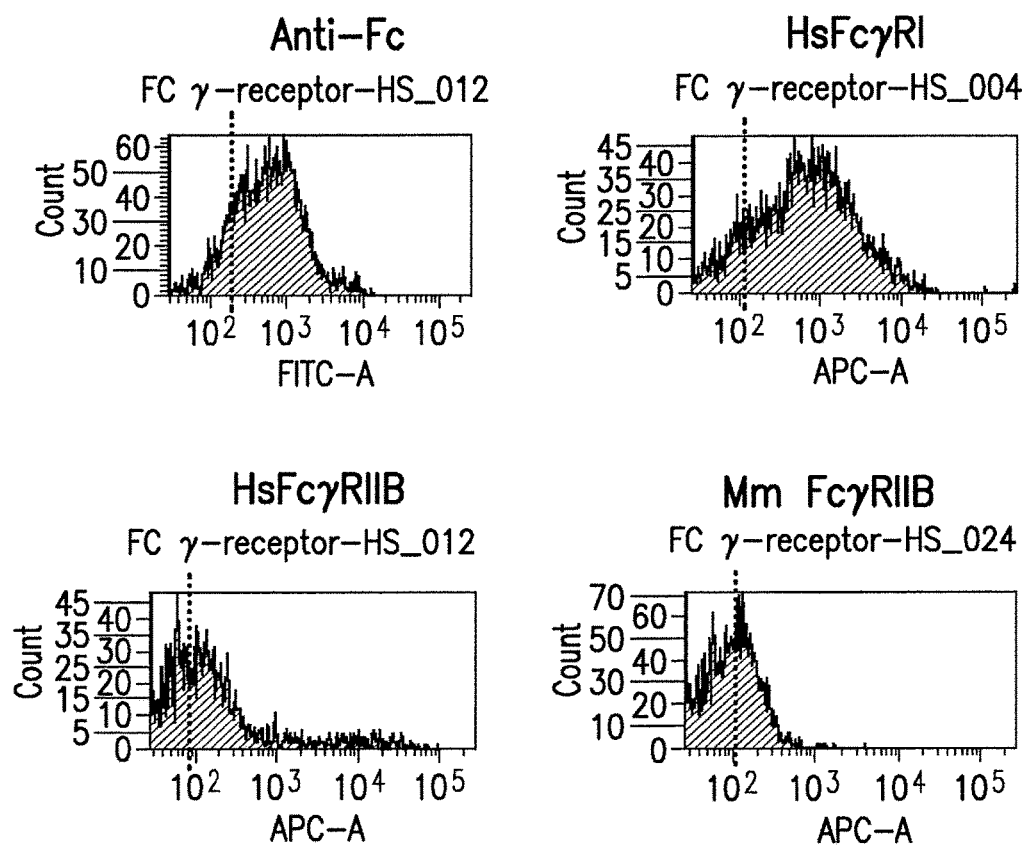

Flow cytometry analysis was conducted using the cells co-expressing Lc-Sed1p bait and anti-Her2 (FIG. 3B), or Lc-Sed1p bait and anti-PCSK9 variants (FIGS. 3C and D). Control was prepared in which an empty strain expressing full length anti-Her2 antibody (H2+L2) only (FIG. 3A) or a strain that expressed the Lc-Sed1p. Strains co-expressing anti-Her2 with the Lc-Sed1p bait (FIG. 3B), or anti-PCSK9 with the Lc-Sed1p bait (FIG. 3C) were found to display significant levels of anti-Fc binding while strains lacking the Lc-Sed1p bait showed background signal levels (FIG. 3A), thus suggesting that Lc-Sed1p bait captured the heavy chain fragment containing the Fc. In FIGS. 3A-D the fluorescent intensities from these experiments were compared. FIG. 3B shows the different fluorescence intensities for anti-Her2 displaying cells while FIG. 3C shows the intensities for the anti-PCSK9 displaying cells, and the parent strains that did not contain the Lc-Sed1p bait (FIG. 3A).

Example 5

Illustration of Display Format for Modulating Binding to Fc Receptors

The display format of the present invention facilitates engineering of the Fc fragment to enable modulating binding to Fc receptors. The binding of Fc receptors to the different displayed IgGs was tested to illustrate this principle. Human Fc gamma Receptor I and Human Fc gamma Receptor IIb were used since they have different affinities to different Fc forms. Mouse Fc gamma Receptor IIb was used as a control. 100 nM of each receptor (His tagged R and D Systems) was incubated at RT for 30 min with a 600 nm optical density of 2 of each culture as described earlier in 100 μL phosphate buffer saline then washed in 100 μl of same buffer. One microliter of FITC conjugated anti-His fragment was added to cells in 100 microliters of PBS and incubated at RT for 15 min. Cells were pelleted washed in 100 microliter PBS and resuspended in 100 microliter PBS before analyzing in a flow cytometric system.

As shown in FIG. 3A, cells from the strain expressing the full length antibody without the Lc-Sed1 system did not stain with anti-His FITC while strains expressing IgGs along with the Lc-Sed1p reacted with anti-His FITC regardless of antibody, IgG type, or glycoform indicating all Fc forms were able to bind Fc gamma Receptor I. These results illustrate that the light and heavy chains were fully assembled on the cell surface.

Figure 3D:
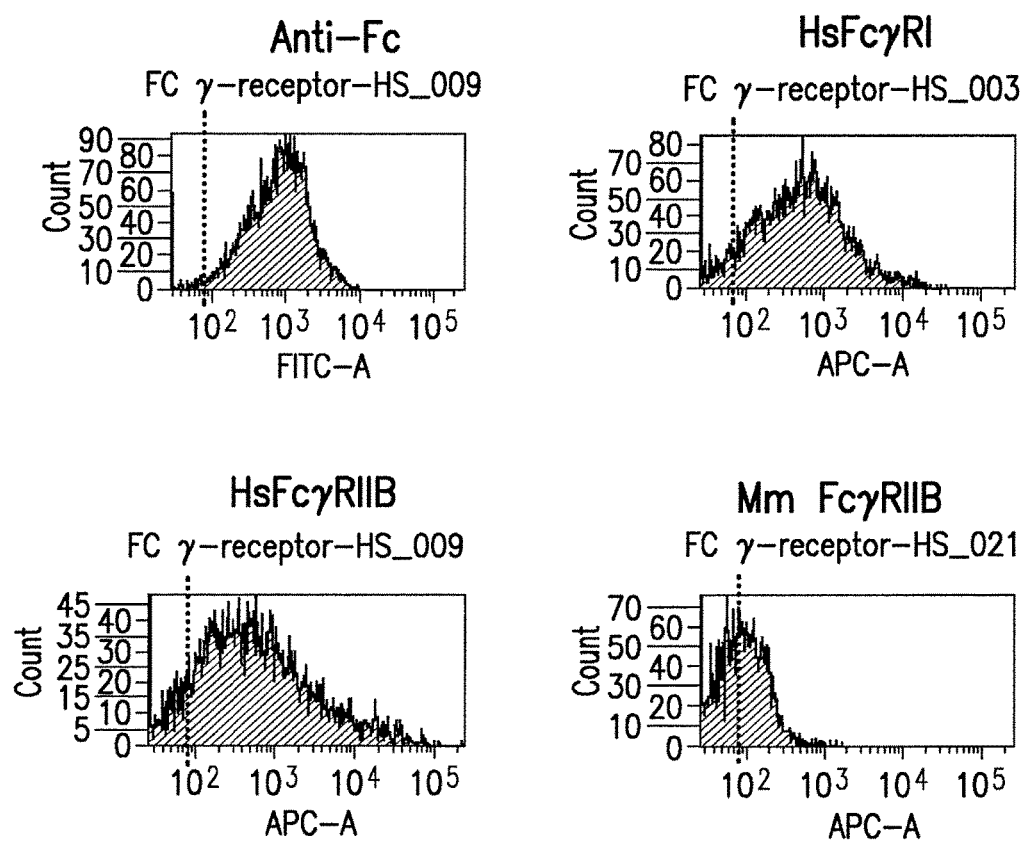

In contrast, only strains containing the four mutations (F243A/V264A/S267E/L328F) in Fc reacted with anti-His FITC suggesting that Fc form was able to bind Fc gamma Receptor IIb (FIG. 3D). This is in agreement with Biacore data obtained from soluble IgGs. This shows that this method can be used to engineer Fc fragments with desirable Fc gamma receptor binding for enhancement of biological and pharmacokinetic properties.

The present invention is not to be limited in scope by the specific embodiments described herein. Indeed, the scope of the present invention includes embodiments specifically set forth herein and other embodiments not specifically set forth herein; the embodiments specifically set forth herein are not necessarily intended to be exhaustive. Various modifications of the invention in addition to those described herein will become apparent to those skilled in the art from the foregoing description. Such modifications are intended to fall within the scope of the claims.

Patents, patent applications, publications, product descriptions, and protocols are cited throughout this application, the disclosures of which are incorporated herein by reference in their entireties for all purposes.

We claim:

1. An antibody display system comprising:
   (a) an isolated host cell, wherein the host cell is a *Pichia* or *Saccharomyces cerevisiae* cell;
   (b) a bait comprising a full-length light immunoglobulin chain fused to a surface anchor polypeptide or functional fragment thereof fused to a signal peptide, wherein the bait polypeptide is located on the extracellular cell membrane surface of the host cell;
   (c) one or more polynucleotides encoding a full-length immunoglobulin light chain;
   (d) one or more polynucleotides encoding a full-length immunoglobulin heavy chain;
   (e) a full-length monovalent antibody comprising two said full-length immunoglobulin heavy chains and two full-length immunoglobulin light chains, wherein the full-length antibody is tethered to the extracellular cell membrane surface of the host cell via the first full-length light immunoglobulin chain fused to a surface anchor polypeptide or functional fragment thereof, wherein the second full-length light chain immunoglobulin chain and both full-length heavy chain immunoglobulin chains are not fused to a surface anchor polypeptide or functional fragment thereof, wherein the second full-length light chain immunoglobulin chain and both full-length heavy chain immunoglobulin chains are encoded by said polynucleotides; and
   (f) a secreted full-length monovalent antibody comprising two said full-length immunoglobulin heavy chains and two said full-length immunoglobulin light chains encoded by said polynucleotides.

2. The antibody display system of claim 1, wherein said one or more polynucleotides encoding an immunoglobulin light chain is from a genetically diverse population of immunoglobulin light chains; and/or,
   wherein said one or more polynucleotides encoding an immunoglobulin heavy chain is from a genetically diverse population of immunoglobulin heavy chains.

3. The antibody display system of claim 1, wherein the host cell comprises a polynucleotide encoding the bait which is operably associated with a regulatable promoter.

4. A method for determining if a full-length antibody, secreted from a host cell, specifically binds to an antigen comprising contacting an antibody display system with said antigen; wherein the antibody display system comprises:
   (a) an isolated host cell, wherein the host cell is a *Pichia* or *Saccharomyces cerevisiae* cell;
   (b) a bait comprising a full-length light immunoglobulin chain fused to a surface anchor polypeptide or functional fragment thereof fused to a signal peptide, wherein the bait polypeptide is located on the extracellular cell membrane surface of the host cell;

(c) one or more polynucleotides encoding a full-length immunoglobulin light chain;
(d) one or more polynucleotides encoding a full-length immunoglobulin heavy chain;
(e) a full-length monovalent antibody comprising two said full-length immunoglobulin heavy chains and two full-length immunoglobulin light chains, wherein the full-length antibody is tethered to the extracellular cell membrane surface of the host cell via the first full-length light immunoglobulin chain fused to a surface anchor polypeptide or functional fragment thereof, wherein the second full-length light chain immunoglobulin chain and both full-length heavy chain immunoglobulin chains are not fused to a surface anchor polypeptide or functional fragment thereof, wherein the second full-length light chain immunoglobulin chain and both full-length heavy chain immunoglobulin chains are encoded by said polynucleotides; and
(f) a secreted full-length monovalent antibody comprising two said full-length immunoglobulin heavy chains and two said full-length immunoglobulin light chains encoded by said polynucleotides; and
determining if a bait/full-length antibody comprising said bait and heavy and light chain immunoglobulins specifically binds, at the cell surface, to said antigen; wherein the secreted full-length antibody is determined to specifically bind said antigen if said bait/full-length antibody specifically binds, at the cell surface, to said antigen.

5. The method of claim 4 further comprising isolating the identified polynucleotides.

6. The method of claim 4 further comprising inhibiting expression of said bait, and determining the affinity of said secreted antibody or antigen-binding fragment thereof for said antigen.

7. The method of claim 4 further comprising recombinantly expressing the immunoglobulin chains encoded by the polynucleotides and, optionally, isolating an antibody or antigen-binding fragment thereof comprising said immunoglobulins and, optionally, producing a pharmaceutical formulation comprising combining said antibody or antigen-binding fragment thereof and a pharmaceutically acceptable carrier.

8. A method for making the antibody display system of claim 1, comprising:
(a) providing an isolated eukaryotic host cell, wherein the host cell is a *Pichia* or *Saccharomyces cerevisiae* cell,
(b) introducing, into said host cell a bait comprising a full-length light immunoglobulin chain fused to a surface anchor polypeptide or functional fragment thereof fused to a signal peptide, wherein the bait polypeptide is located on the extracellular cell membrane surface of the host cell; and
(i) one or more polynucleotides encoding a full-length immunoglobulin light chain; and
(ii) one or more polynucleotides encoding a full-length immunoglobulin heavy chain.

9. A method for making a full-length antibody comprising:
(a) providing an isolated eukaryotic host cell, wherein the host cell is a *Pichia* or *Saccharomyces cerevisiae* cell,
(b) introducing, into said host cell a bait comprising a full-length light immunoglobulin chain fused to a surface anchor polypeptide or functional fragment thereof fused to a signal peptide, wherein the bait polypeptide is located on the extracellular cell membrane surface of the host cell; and
(i) one or more polynucleotides encoding a full-length immunoglobulin light chain; and
(ii) one or more polynucleotides encoding a full-length immunoglobulin heavy chain; and culturing the host cell under condition whereby the polynucleotides encoding the immunoglobulin chains are expressed and an antibody or antigen-binding fragment thereof is formed from said chains; wherein said bait is operably associated with a regulatable promoter and bait expression is inhibited when said immunoglobulin chains are expressed.

10. A method for determining the effect of a sugar on a full-length antibody which specifically binds to an antigen comprising contacting an antibody display system with said antigen; wherein the antibody display system comprises:
(a) an isolated host cell, wherein the host cell is a *Pichia* or *Saccharomyces cerevisiae* cell;
(b) a bait comprising a full-length light immunoglobulin chain fused to a surface anchor polypeptide or functional fragment thereof fused to a signal peptide, wherein the bait polypeptide is located on the extracellular cell membrane surface of the host cell;
(c) one or more polynucleotides encoding a full-length immunoglobulin light chain;
(d) one or more polynucleotides encoding a full-length immunoglobulin heavy chain;
(e) a full-length monovalent antibody comprising two said full-length immunoglobulin heavy chains and two full-length immunoglobulin light chains, wherein the full-length antibody is tethered to the extracellular cell membrane surface of the host cell via the first full-length light immunoglobulin chain fused to a surface anchor polypeptide or functional fragment thereof, wherein the second full-length light chain immunoglobulin chain and both full-length heavy chain immunoglobulin chains are not fused to a surface anchor polypeptide or functional fragment thereof, wherein the second full-length light chain immunoglobulin chain and both full-length heavy chain immunoglobulin chains are encoded by said polynucleotides; and
(f) a secreted full-length monovalent antibody comprising two said full-length immunoglobulin heavy chains and two said full-length immunoglobulin light chains encoded by said polynucleotides; wherein said heavy or light chain comprises said sugar; determining if said bait/full-length antibody specifically binds to said antigen; determining the binding affinity of the full-length antibody comprising said sugar for the antigen; and comparing the affinity of the full-length antibody with affinity of an otherwise identical full-length antibody which lacks said sugar; wherein the sugar is determined to increase affinity for the antigen if the affinity of the full-length antibody comprising said sugar is higher than the affinity of the full-length antibody which lacks the sugar, and/or wherein the sugar is determined to decrease affinity for the antigen if the affinity of the full-length antibody comprising said sugar is lower than the affinity of the full-length antibody which lacks the sugar.

11. A method for determining the whether an mutation in an immunoglobulin heavy chain Fc region increases or decreases binding of said chain to an Fc receptor or to a lectin comprising contacting an antibody display system with said Fc receptor or lectin; wherein the antibody display system comprises:
(a) an isolated host cell, wherein the host cell is a *Pichia* or *Saccharomyces cerevisiae* cell;

(b) a bait comprising a full-length light immunoglobulin chain fused to a surface anchor polypeptide or functional fragment thereof fused to a signal peptide, wherein the bait polypeptide is located on the extracellular cell membrane surface of the host cell;
(c) one or more polynucleotides encoding a full-length immunoglobulin light chain;
(d) one or more polynucleotides encoding a full-length immunoglobulin heavy chain;
(e) a full-length monovalent antibody comprising two said full-length immunoglobulin heavy chains and two full-length immunoglobulin light chains, wherein the full-length antibody is tethered to the extracellular cell membrane surface of the host cell via the first full-length light immunoglobulin chain fused to a surface anchor polypeptide or functional fragment thereof, wherein the second full-length light chain immunoglobulin chain and both full-length heavy chain immunoglobulin chains are not fused to a surface anchor polypeptide or functional fragment thereof, wherein the second full-length light chain immunoglobulin chain and both full-length heavy chain immunoglobulin chains are encoded by said polynucleotides; and
(f) a secreted full-length monovalent antibody comprising two said full-length immunoglobulin heavy chains and two said full-length immunoglobulin light chains encoded by said polynucleotides; and determining if said bait/full-length antibody specifically binds to said Fc receptor or lectin; and determining the binding affinity of the full-length antibody for the Fc receptor or lectin; and comparing the affinity of the full-length antibody with affinity of an otherwise identical full-length antibody which lacks said mutation; wherein the mutation is determined to increase affinity of the heavy chain for the Fc receptor or lectin if the affinity of the full-length antibody comprising said mutation is higher than the affinity of the full-length antibody which lacks the mutation, and/or wherein the mutation is determined to decrease affinity for the Fc receptor or lectin if the affinity of full-length antibody comprising said mutation is lower than the affinity of the full-length antibody which lacks the mutation.

* * * * *